United States Patent
Mazzocchi et al.

(10) Patent No.: US 9,532,902 B2
(45) Date of Patent: Jan. 3, 2017

(54) MINIMALLY-INVASIVE METHOD AND APPARATUS FOR RESTRUCTURING THE RETINA

(75) Inventors: Rudy A. Mazzocchi, Rockledge, FL (US); Michael Calhoun, Lighthouse Point, FL (US)

(73) Assignee: Optistent, Inc., Coral Springs, FL (US)

( * ) Notice: Subject to any disclaimer, the term of this patent is extended or adjusted under 35 U.S.C. 154(b) by 39 days.

(21) Appl. No.: 13/579,312

(22) PCT Filed: Feb. 22, 2011

(86) PCT No.: PCT/US2011/025686
§ 371 (c)(1),
(2), (4) Date: Oct. 3, 2012

(87) PCT Pub. No.: WO2011/103555
PCT Pub. Date: Aug. 25, 2011

(65) Prior Publication Data
US 2013/0046382 A1 Feb. 21, 2013

Related U.S. Application Data

(60) Provisional application No. 61/306,644, filed on Feb. 22, 2010.

(51) Int. Cl.
*A61F 2/16* (2006.01)
*A61F 9/007* (2006.01)
*A61F 9/00* (2006.01)

(52) U.S. Cl.
CPC ......... *A61F 9/00727* (2013.01); *A61F 9/0017* (2013.01); *A61F 2210/0019* (2013.01)

(58) Field of Classification Search
CPC .......... A61F 2/14; A61F 9/08; A61F 9/00727; A61N 1/0543; A61N 1/36046
(Continued)

(56) References Cited

U.S. PATENT DOCUMENTS 5,846,258 A 12/1998 Takayanagi et al.
6,699,285 B2 * 3/2004 Zapata .................. 623/6.63
(Continued)

FOREIGN PATENT DOCUMENTS

CN 101049270 A 10/2007
DE 3640013 A1 5/1988
(Continued)

OTHER PUBLICATIONS

European Search Report dated Aug. 1, 2014, EP Appl No. 11745421.5.
(Continued)

*Primary Examiner* — David H. Willse
*Assistant Examiner* — Tiffany Shipmon
(74) *Attorney, Agent, or Firm* — Keller Life Science Law, P.A.

(57) ABSTRACT

The present invention comprises an implant for placing inside the eye such that the implant comes into contact with the interior tissue of the eye such that it conforms to the inner globe geometry of the eye. Implants of the present invention may also be used to alter the focal length of the eye thereby providing a treatment method for the correction of myopia and hyperopia. The device may consist of several possible configurations, an open mesh structure, a solid metal ring, a solid polymer shape, a mesh polymer shape or combination of these. The shape may be a curve, a sphere, a ring or a combination thereof that are specifically shaped to approximate a desired portion of the interior globe of the eye in order to treat myopia or hyperopia.

37 Claims, 9 Drawing Sheets

(58) Field of Classification Search
 USPC .................................................. 623/4.1, 6.63
 See application file for complete search history.

(56) References Cited

U.S. PATENT DOCUMENTS

| | | |
|---|---|---|
| 6,786,927 B2 | 9/2004 | Pallikaris et al. |
| 6,793,674 B2 | 9/2004 | Zapata |
| 2001/0008978 A1 | 7/2001 | Zapata |
| 2002/0055701 A1* | 5/2002 | Fischell et al. ................. 602/47 |
| 2004/0097957 A1 | 5/2004 | Jaker et al. |
| 2009/0196903 A1 | 8/2009 | Kliman |

FOREIGN PATENT DOCUMENTS

| | | |
|---|---|---|
| JP | 10179629 | 7/1998 |
| WO | 2009037384 A1 | 3/2009 |

OTHER PUBLICATIONS

International Search Report and Written Opinion dated Aug. 28, 2012, PCT/US2011/025686, filing date Feb. 22, 2011.

* cited by examiner

MINIMALLY-INVASIVE METHOD AND APPARATUS FOR RESTRUCTURING THE RETINA

This application claims priority to U.S. provisional patent application No. 61/306,644 filed on Feb. 22, 2010, the contents of which are expressly incorporated herein by reference.

The retina is the interior layer of the posterior eyeball. The retina receives images as they enter through the lens, is continuous with the optic nerve, and consists of several layers, one of which contains the rod cells and cone cells that are sensitive to light.

A retinal detachment is a separation of the retina from its attachments to the underlying supporting choroid tissue within the eye. Most retinal detachments are a result of an opening that originates as a retinal break, hole, or tear. This opening can allow vitreous humor fluid to leak in between the retina and the choroid tissue. In areas where the retinal tissue is thin or weak, it can also tear. This fluid infiltration forces the retina away from the choroid causing blind spots where the retina has separated. This is referred to as a retinal detachment. As more fluid collects behind the retina, the extent of the retinal detachment can progress and possibly involve the entire retina, which can lead to a total detachment with corresponding vision loss.

A retinal detachment is commonly preceded by a posterior vitreous detachment which may result in photopsia (flashes of light in the peripheral vision), floaters (deposits within the vitreous) or feelings of heaviness in the eye. As it retina begins to detach a person will usually experience a shadow originating in the peripheral vision and moving into the center of the visual field as the detachment progresses; cloudiness in their vision; distortion of straight lines and visual loss.

Current Methods of Treatment

Retinal holes or tears can be treated with diathermy (heating), laser (heating) or cryotherapy (freezing) to prevent their progression to a full-scale detachment. Many factors determine which holes or tears need to be treated. These factors include the type and location of the defects, whether pulling on the retina (traction) or bleeding is involved, and the presence of any of the other risk factors discussed above. Several types of eye surgery are done for repair of retinal detachment. These include: scleral buckling, pneumatic retinopexy, vitrectomy, silicone oil injection and perfluoron liquid injection.

Retinal tears as well as complicated or severe retinal detachments typically require an operation called a vitrectomy prior to performing specific treatment on the retina. These retinal tears and/or detachments include those that are caused by the growth of abnormal blood vessels on the retina or in the vitreous, which often occurs as a complication of advanced diabetes. Vitrectomy is also typically used with giant retinal tears, vitreous hemorrhage (blood in the vitreous cavity that obscures the surgeon's view of the retina), extensive tractional retinal detachments (pulling from scar tissue or vitreous humor), membranes (extra tissue) on the retina, or severe infections in the eye (endophthalmitis). Vitrectomy surgery is performed in the hospital under general or local anesthesia. Small openings are made through the sclera to allow positioning of a fiberoptic light, a cutting source (specialized scissors), and a delicate forceps. The surgeon identifies the retinal holes or tears either through an operating microscope or a focusing headlight (indirect ophthalmoscope). The vitreous fluid of the eye is removed and the immediate area of the retinal tear is treated with either diathermy (heating), cryo (freezing) or laser (heating) procedures such that the retinal tissue is scarred. This scarring re-attaches the damaged area of the retina to the underlying tissue. This fixation is intended to prevent further immediate tearing in the area treated. In order for the retina to fully heal and reattach, there are several methods used to provide longer term therapy. These include pneumatic retinopexy (insertion of a gas bubble), scleral buckling (band around the outside of the eye), injection of silicone oil or injection of perfluoron liquid into the interior of the eye. Each of these methods is designed to provide long term support of the retina so that healing may take place.

Silicone oil may stay in place for up to eight months and requires a subsequent surgical intervention to remove the fluid. There are different viscosities of silicone oil available and the use depends on the specifics of the detachment. Vision is compromised during the time silicone is in the eye Perfluoron is a fluid that is typically used on a short term basis and must be removed via a subsequent surgical intervention. This fluid is typically used during the surgical procedure to provide immediate tamponade and is typically exchanged for silicone oil. Perfluoron can be used for several days, but is not intended to be left in the eye for extended periods of time.

Patients who undergo Pneumatic Retinopexy are injected with a gas bubble that puts pressure against the retina to hold it in place while re-attachment occurs. These patients are required to sleep face-down or on one particular side for several days (up to one month) to ensure the gas bubble applies pressure to the appropriate segment of the retina. Some of their daily activities must be completed with the patient in an essentially head down position. Vision is completely absent or totally blurred for a period of several weeks prior to the dissolution of the bubble.

For many years, scleral buckling has been the standard treatment for detached retinas in areas with modern medical care. The surgery is done in a hospital operating room with general or local anesthesia. A scleral buckle, which is made of silicone, plastic, or sponge, is then sewn to the outer wall of the eye (the sclera). The buckle is like a tight cinch or belt around the eye which compresses the eye so that the hole or tear in the retina is pushed against the outer scleral wall of the eye, which has been indented by the buckle. The buckle may be left in place permanently. It usually is not visible because the buckle is located halfway around the back of the eye (posteriorly) and is covered by the conjunctiva (the clear outer covering of the eye), which is carefully sewn (sutured) over it. Compressing the eye with the buckle also reduces any possible later pulling (traction) by the vitreous on the retina. Scleral buckles may be performed with or without vitrectomy. One of the side effects of using scleral buckles is that they alter the shape of the eye and can make a patient more near sighted after the surgery.

U.S. Pat. No. 6,699,285 describes an implanted structural band that is delivered through a syringe type injector. This band is constructed of a plastic or rubberlike material, or a rubber-covered wire, that is flexible enough to be inserted to match the curvature of the eye (having a length of at least 100 degrees of the circumference of the globe). Upon insertion the band exerts a pressure against the retina thereby pressing the retina into the globe of the eye. The device may contain a pair of curled ends to prevent penetration of the retina during implantation. The requirement that the band be greater than 100 degrees ensures that the device will bend to create a pressure sufficient to press the retina into the globe of the eye. A downside to this approach is that it will obscure vision and the band is likely to be difficult to place.

SUMMARY OF THE INVENTION

The present invention is a method and mechanical means to apply a structure, which can be designed to be permeable to light and fluid, to the back portion of the eye to hold the retina in place. There may be situations where the device, in whole or part, may not need to provide permeability to light and fluid. It is believed that this support structure will induce re-attachment of the retina to the posterior portion of the globe restoring some level of vision and preventing further damage to the retina and additional loss of vision.

Devices of the present invention can be formed from a resilient shape-memory material such as a metal or a polymer that can be stored and deployed in one configuration but upon deployment assume a stable desired configuration. Such devices are commonly used in the cardiology and peripheral vasculature fields to open vessels or to capture particles in circulating fluid but are not known for use within delicate organs such as the eye.

This device will be placed by creating an incision through the sclera into the anterior chamber and inserting a delivery system containing the device in a collapsed state. The surgeon will typically look through the lens of the patient's eye and position the device, over the retinal tear. The device will then be delivered to the site, disengaged from the delivery system and manipulated and fixed in the desired location. The delivery system will be removed and the incision will be closed. The device will remain in place on either a temporary or permanent basis to aid in the re-attachment of the retinal tissue.

DETAILED DESCRIPTION OF THE INVENTION

Figure 5:
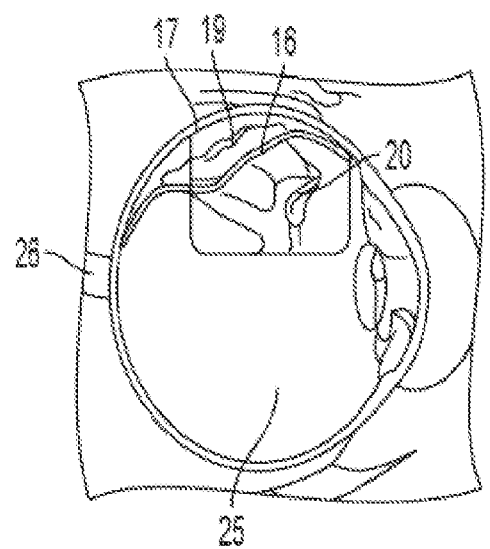
FIG. 5 is a drawing of a retinal tear.

A retinal detachment is a separation of the retina from its attachments to its underlying supporting choroids tissue within the eye. Most retinal detachments are a result of an opening in the retinal wall due to a break, hole, or tear. The opening in the retina may allow the vitreous humor fluid to get in between the retina and the choroid. The fluid can force the retina away from the choroid causing blind spots where the retina has separated. Where the retina is weak, it will tear. As more of the vitreous collects behind the retina, the extent of the retinal detachment can progress and possibly involve the entire retina, leading to a total retinal detachment. A representative tear 20 is shown in FIG. 5 in which the retina 16 has separated from the underlying supporting choroid tissue 17. The tear 20 allows fluid 19 from the posterior chamber 25 to penetrate behind the retina 16 thereby separating the retina 16 from the underlying optic nerve 26. As fluid 19 builds up, the detachment gradually gets larger leading to progressive, and in some cases, total loss of vision Implants of the present invention comprise a device sized to fit inside the posterior chamber of the eye and is specifically shaped to be positionable over the retina. When positioned, the device may have a means to allow for transmission of light to the retina, the mechanism for this transmission may be in the material spacing, material composition or combination of both. Such implants can be constructed of a variety of materials. These may include braided metal fabric, stamped or machined metal or woven or molded polymer, or combination thereof, any of which have may have shape memory and/or superelastic properties. Such devices would be made available in a variety of curved diameters representing conical sections that are either semi-circular, elliptical, parabolic or hyperbolic, and specifically selected according to the location, size and or severity of the detachment. This device may not restore loss of vision due to previous retinal damage, but would be intended to prevent further loss of vision due to detachment and would provide a therapeutic option which may provide a faster recovery time as compared to current conventional therapies.

An implant comprising a substantially hemispherical, semi-circular shape may yield the highest retention forces, facilitate alignment and/or prevent mis-alignment of the device one in place. Typically, the degrees of coverage envisioned would be in the 220° to 270° range. Extending from the macula in a direction towards the anterior section of the eye, the device would extend approximately 110° to 135° in each direction until the anterior border of the retina. The device could be manufactured to provide varying degrees of coverage, depending on the specific need and these could be substantially larger or smaller that the 270° as mentioned. In some cases, the device could be constructed as a spheroid (360°) which would provide for some degree of light transmission, while being designed to not come into direct contact with the corneal area. Other cases may involve the fabrication of an essentially spheroid device (360°) that does not allow for the transmission of light. In these instances, the focus of the device would be to provide therapy in cases of extreme detachment. This version of the device would be intended to treat persons with recurrent detachments and the focus would be on saving the sight of the eye long term without providing sight during recovery. However, devices comprising shorter curves may be preferred in at least certain instances to minimize the surface contact of the implant against normal, healthy areas of the retina. The implant will require specific sizing to produce sufficient forces to hold the retina in place for the duration of its intended use. In some instances, it is contemplated that the implant may be permanent. In other instances, the implant may be designed to be removable after the retina has reattached. Other embodiments may be designed to be absorbed over time. Some embodiments may be coated or loaded with a drug(s) that provides therapeutic value for a specified period of time or designed to release drugs in s specified sequence according to therapeutic regime. Other embodiments may include a device to be placed in the eye and then loaded with drug(s) by the surgeon. This particular embodiment may also provide the device with the ability to be reloaded by the surgeon over a period of time to facilitate a specific therapy. This embodiment may also be loaded with one or more drugs in separate chambers so as to perform a desired release pattern to achieve a specific therapeutic regime.

One class of materials which meet the design requirements for certain embodiments of the device are so-called shape memory metallic alloys. Such alloys are fabricated to have a temperature induced phase change which will cause the material to exhibit a preferred configuration. This configuration can be fixed or set by heating the material above a certain temperature to induce a change in the phase of the material. When the alloy is cooled back down, the alloy will "remember" the shape it was in during the heat treatment and will tend to assume or transition back to that configuration once a certain temperature is reached. The device can be prevented from undergoing this transition is some cases, such as when loaded into a delivery device.

One particularly preferred shape memory metallic alloy for use in the present method is nitinol (NITI), an alloy of nickel and titanium. NiTi alloys, including appropriate compositions and handling requirements, are well known in the art and such alloys need not be discussed in detail here. For example, U.S. Pat. Nos. 5,067,489 (Lind) and 4,991,602 (Amplatz et al.) and 6,797,083 (Peterson) the teachings of which are incorporated herein by reference, discuss the use of shape memory NiTi alloys in guidewires and other devices. Such NiTi alloys are preferred, at least in part, because they are commercially available, more is known about handling such alloys than other known shape memory alloys and biocompatibility is well established. NiTi alloys also exhibit very elastic characteristics—they are sometimes referred to as "superelastic" or "pseudoelastic" materials. This elasticity will help a device of the invention return to a present expanded configuration after deployment and may also aid in removal if necessary.

When manufacturing the device of bioabsorbable materials, any known bioabsorbable material which is safe for use in living organisms may be used. Suitable bioabsorbable materials include (e.g., a bioerodible metal, a bioerodible polymer, a bioerodible ceramic, and/or a bioerodible metal salt). Examples of bioabsorbable metals suitable for use in the body include magnesium, iron, zinc, and alloys thereof. An example of a suitable bioabsorbable iron alloy includes Fe-35 Mn. Examples of bioabsorbable polymers suitable for use as the body 30 include polyglutamic acid, polylactic acid (PLA), poly(ethylene oxide) (PEO), poly-serine, polycaprolactam, poly(lactic-co-glycolic acid) (PLGA), cyclodextrins, polysaccharides (e.g., chitosan and hyaluronan), copolymers thereof, and combinations thereof. Other examples of bioabsorbable polymers include polyglycolic acid (PGA), polycaprolactone (PCL), polyorthoesters, polydioxanone, poly (trimethylene carbonate) (PTMC), polyphosphazenes, polyketals, proteins (e.g., glycoproteins, fibrin, collagen, gelatin, pectin), polyanhydrides (e.g., poly(ester anhydride)s, fatty acid-based polyanhydrides, amino acid-based polyanhydrides), polyesters, polyester-polyanhydride blends, polycarbonate-polyanhydride blends, and/or combinations thereof. The bioabsorbable polymers can be blended and/or copolymerized to alter the degradation characteristics. Poly-L-lactic acid is particularly suited for manufacture of devices of the present invention.

In certain embodiments the use of shape memory polymers may be desired. U.S. Pat. No. 6,720,402, the contents of which are incorporated herein, describes certain shape memory polymers which would be useful in making implants of the present invention One such method of making the device follows: After the desired shape is fabricated, the resulting shaped material is deformed using a mold or die to achieve a contracted state. The deformed state is set by heating the mold and the material using time and temperature of the heat treatment to substantially set the material in its deformed state. After the heat treatment, the material is removed from contact with the molding element and will substantially retain the deformed state. The material so treated defines a collapsed state of a medical device which can be deployed through a delivery device into the desired position in a patient's body. The general intra ocular pressure (IOP) of a normal human eye is in the 10 to 21 mmHg range. This value converts to approximately 0.19 to 0.41 psi. It is thought that the device will need to exhibit slightly more force than that of a normal range IOP value so that the device will be held in place while providing adequate support to aid in the therapeutic re-attachment of retinal tissue. It is also thought that the force may be modified in such a fashion as to vary along the device or to be higher or lower overall. It would also be possible to vary the degree of force along a single implant. These modifications could be necessary in special cases, such as extreme, severe or recurrent cases of detachment.

The device may consist of a braided or woven metal fabric, a metal sheet, a metal wire, polymeric sheet, polymeric strands or combination thereof that exhibit shape memory, biodegradeable and/or superelastic properties. The device can be either either in a single layer, inverted spherical double layer or multiple layer designs that would be made available in a variety of curved diameters representing conical sections that are either semi-circular, elliptical, parabolic or hyperbolic, and selected according to the location and size of the detachment The semi-circular shape may yield the highest retention forces and prevention from misalignment, but smaller curves may be preferred to minimize the surface contact of the implant against normal, healthy areas of the retina.

The device may include a means of attachment that will allow the surgeon to manipulate the implant into proper position prior to releasing it into its desired location. One particular embodiment shall enable the collapse and withdraw of the implant as long as it is securely attached to the delivery system. Such an embodiment shall include a larger co-axial cannula system that can be advanced over the introducer cannula to maximize the inner diameter of a system that allows for withdraw of the collapsed device.

One such embodiment of the design may use braided material. In this case, the material shall be constructed of a wire diameter sufficient to provide adequate retention pressure against the retina, but small enough to optimize the openings in the metal fabric that are regulated by the "pic" and "pitch" of the braid. This braiding parameter is also important to allow for maximum light absorption to pass through to the retina. Wire diameters may, range, but are not limited to, from 0.0005 to 0.010 inches, with the a preferred diameter in the 0.001-0.003 inch range.

The device may comprise a self-expanding metal or polymer in the form of a weave, braid, single, multi-stranded composite or combination material with a porosity sufficient as to maintain structural integrity but porous enough as to not inhibit images or light to reach the photoreceptors of the retina. (Similar to looking through a screen door or window.) Such a polymer embodiment may be translucent to minimize the effect of potential interference of light transmission and/or may be made of a biodegradeable material which degrades (dissolves) after sufficient time to allow for re-attachment. There may also be a device comprised of a combination of metallic and polymeric materials. In certain embodiments, there may be no need to allow for the transmission of light.

The device shall be constructed of the appropriate diameter, thickness or durometer of wires, fabric strands, polymer or other material with a defined "tension" that properly applies sufficient radial pressure to the retinal wall. The device may also be designed such that it does not bond with the retinal tissue, promote tissue ingrowth or membrane growth. This characteristic may be achieved through several methods which include, natural material characteristics, anti stick coating such as ptfe, surface modifications, pharmaceutical agents, etc.

The device may be permanent or temporarily placed long enough to allow for therapeutic treatment of the retina and include a means by which the device can be retrieved, re-aligned or reloaded with drugs as necessary. The device may also be placed in the eye on a permanent basis.

More than one device may be placed in the eye. Use of multiple devices may encompass devices of the same material or devices of different materials. These multiple devices may be arranged such that they are removed at the same or different times, depending on the specifics of therapy (ie: re-attachment of the retina, delivery of drugs, etc).

One preferred embodiment may include an eyelet, bead or closed loop that can be captured and contained in order to retrieve or re-align the position of the implant through a small diameter cannula placed from outside the eye.

Another embodiment of a temporary device may include a small fine filament or suture that is attached to the lateral side of the device to function as a "tether" that exits the orbital of the eye for extraction at a later date following re-attachment of the retina.

In yet another embodiment of the implant, hooks, scales or barbs are provided on the surface of the device as a means of secondary attachment. The hooks, scales or barbs may be located anywhere along the surface. Alternatively the implant can be attached to the wall of the eye by use of sutures, lasers, cryo, adhesive or mechanical means.

Figure 3:
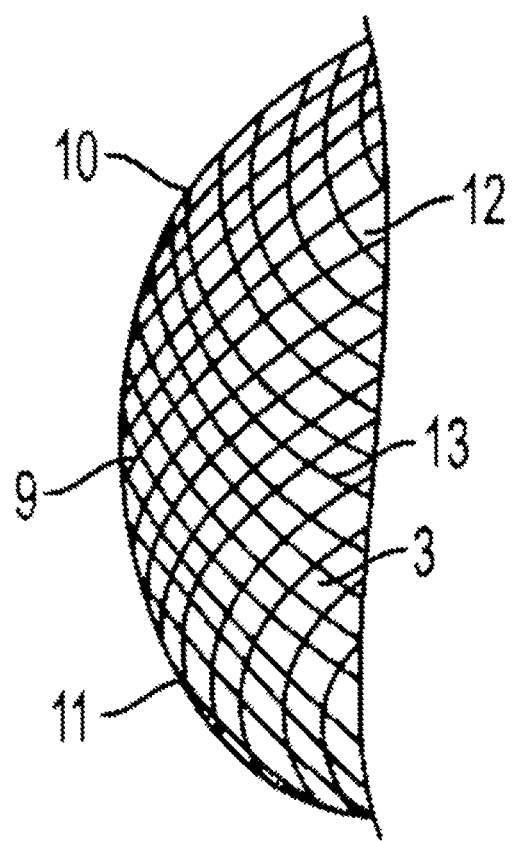
FIG. 3 is a side view of a device of the present invention

Referring now to FIG. 3, which shows a side view of an implant 10 of the present invention. The implant comprises a curved end 11 which when placed abuts the retina, an open end 13 which is open to the posterior chamber of the eye. The implant is comprised of structural elements 12 which define a mesh 9 having openings 3 through which light can pass. It will be appreciated that the shape of the device can be any structure which conforms to the location of the retinal tear and is capable of providing sufficient pressure to hold the retina in its undamaged position. Contemplated within the scope of this invention are conical sections that are either semi-circular, elliptical, parabolic or hyperbolic. This particular embodiment may also have a hole woven into the area around 9, such that there is no material obscuring the fovea/macula. It is also anticipated that the device could be fabricated such that other anatomical landmarks of the eye could be selectively covered or not, depending on need. The structural element 12 may also extend in the anterior direction of the interior chamber such that it terminates at the anterior retinal border or beyond. It is also anticipated that the device could be essentially spheroid in construction as noted in FIG. 11C and could be designed such that it does not touch the corneal tissue. The spheroid design could be fabricated such that light transmission may or may not be possible.

Figure 1:
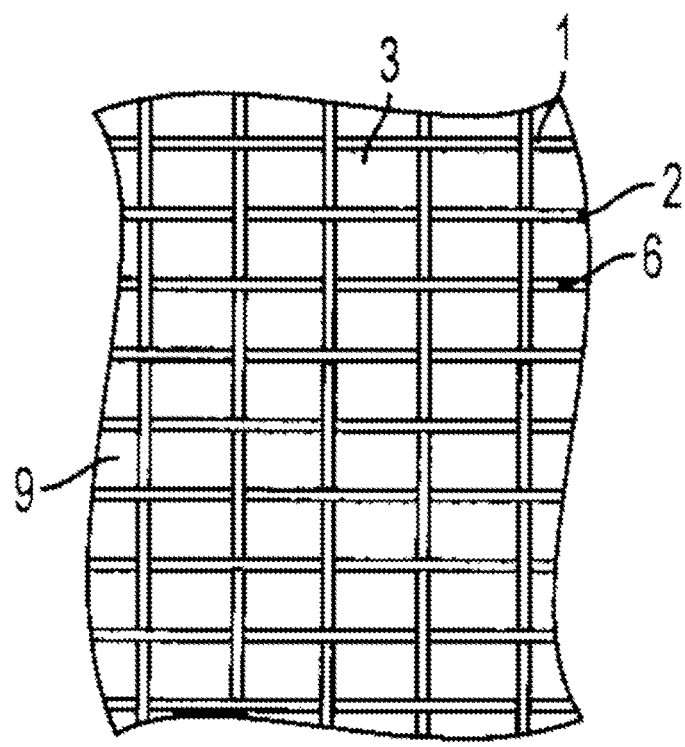
FIG. 1 shows a possible weaving pattern for devices of the present invention

Referring to FIG. 1, the present invention is comprised of a mesh 9 having sufficient openings in the structure to allow light to pass through. FIG. 1 shows a metal fabric formed of a plurality of vertical strands 1 which are woven through a plurality of horizontal strands 2 in an over and under fashion 6. The weave produced has openings 3 through which light can pass. The resulting fabric can be heat treated to substantially set a desired expanded shape. U.S. Pat. No. 7,367,985, which is incorporated by reference, describes such a process for creating woven structures of the type contemplated by this invention.

Figure 2:
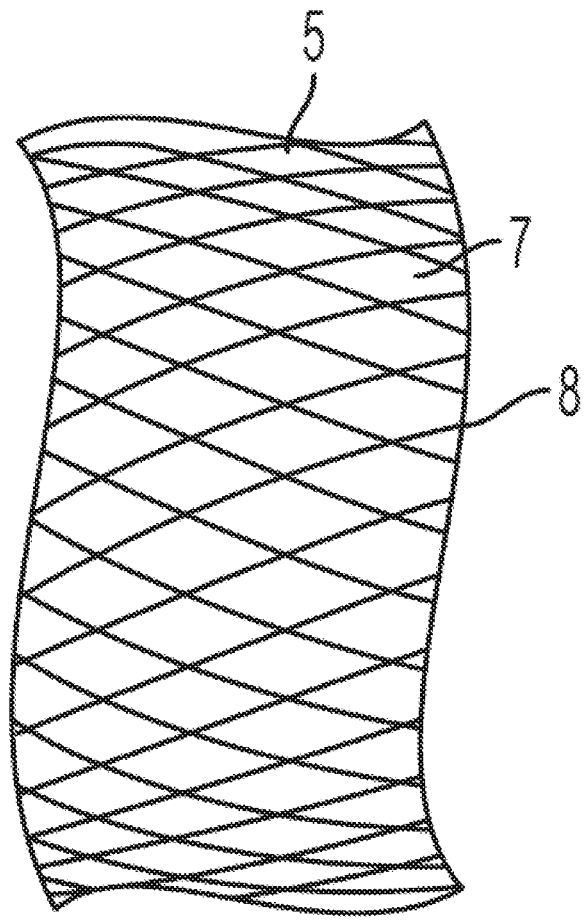
FIG. 2 shows a second possible weaving pattern for devices of the present invention.

FIG. 2 shows another weave of the fabric in FIG. 1 in which the fabric is woven on a diagonal.

Figure 4:
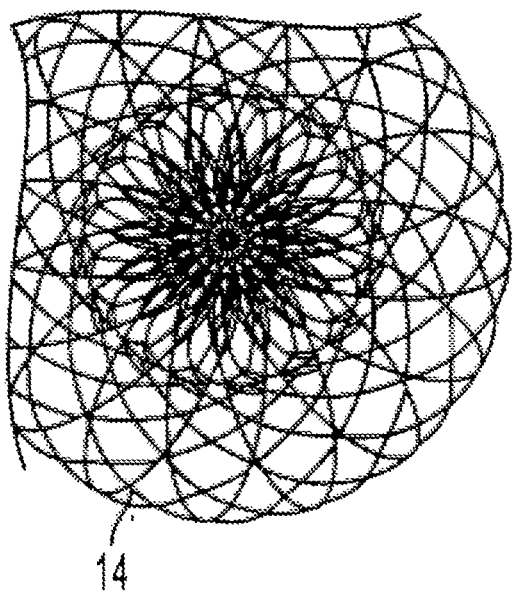
FIG. 4 is a top view of a device of the present invention

FIG. 4 shows yet another embodiment of the device having a more complex woven pattern woven which lacks free ends.

FIG. 5 is a drawing of a retinal tear.

Figure 6:
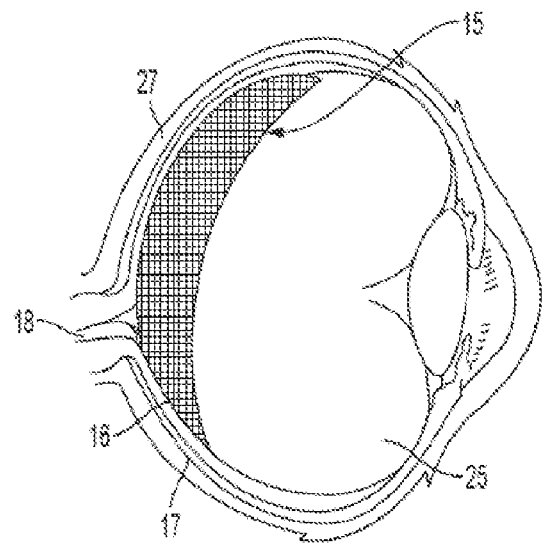
FIG. 6 is a drawing showing placement of the device of the present invention over a retinal tear.
Figure 7A:
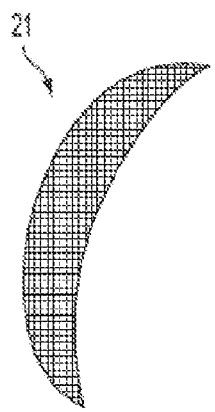
FIGS. 7 *a-d* show variations in shape and size of the present invention.
Figure 7B:
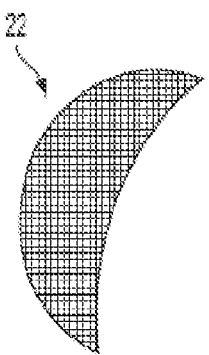
Figure 7C:
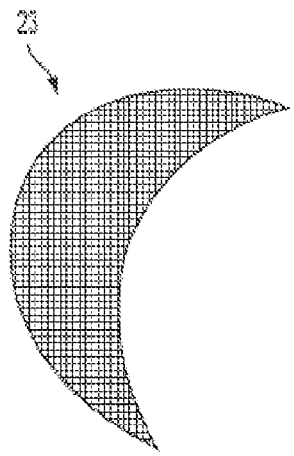
Figure 7D:
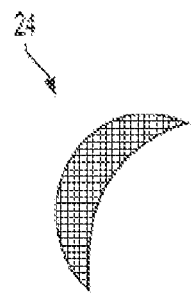

FIG. 6 shows an implant 15 of the present invention positioned inside the posterior chamber 25 against the retina 16. In this figure, the retinal tear 20 (not shown) has been pressed back into position.

FIGS. 7 A through D show varying shapes of an implant 15 of the present invention.

It is not believed that anchoring the device to the eye with any means other than the outward force of the implant will be necessary. However, should the need arise in which movement of the implant needs to be prevented it may be desirable to provide a means for anchoring the device in the eye. This can be accomplished through any means which is acceptable for an implanted device. Retinal tacks have long been used to repair a detached retina and may be incorporated into the present device or used as separate elements. An example of a retinal tack is disclosed in U.S. Pat. No. 4,712,550, the contents of which are expressly incorporated herein by reference. In some instances it may be desirable to build an anchor into the stent such that when it is deployed the anchor embeds in the tissue. In other instances, it may be sufficient to use a suture through the body of the stent to anchor it in a given location. In instances where the anchor is part of the device, the anchor can be used for delivery of medication in tissues In yet another embodiment, the device can be manufactured from a shape memory polymer as disclosed in U.S. Pat. No. 6,720,402 which is expressly incorporated herein by reference. An advantage to using polymers instead of metals is that polymers can be readily molded and specifically designed to have a high water content. Another advantage is that the implant can be made to be absorbed after insertion and thereby avoid long term complications from an implant. Polymers can also be chosen for their transparency to allow for greater light transmission. Polymers could also be made to contain and dispense drugs in a desired fashion. The polymer design could also be made of a hydrogel (or equivalent) material so as to minimize the possibility of adhesion or disruption of the retinal tissue. This polymer design could be made so as to have a preferred refractive index for allowing light transmission to the retinal tissue so as to provide vision. The polymer design may also be manufactured with a variety of surface shapes so as to allow for selective contact between the retinal tissue bed with vitreous humor fluid. This polymer design could also include a provision of accommodating a pharmaceutical in an arrangement similar to a reservoir. This pharmaceutical could be placed in the device prior to delivery, or inserted after the device has been placed. This polymer reservoir design could also provide the capability for a retinal surgeon to periodically place additional medicaments in the reservoir (of the same or different constituents) for the treatment of the retinal tissue bed. In the case of a drug eluting design, the device could be designed so as to direct drug elution into retinal tissue and prevent elution into the eye cavity. As shown in U.S. Pat. No. 6,720,402 the polymers can be designed to be collapsed at cooler temperatures and to unfold at body temperatures. The polymers could also be made from different layers, material durometers and may incorporate metallic or polymetric stiffening elements. There could also be a provision to allow for more than one device to be installed and as the patient improves, layers could be removed as desired until there were no layers left.

In yet another embodiment, the implant further comprises a loop or eyelet which can be grabbed by a guidewire or loop snare and used to retrieve the implant into a cannula for removal from the eye.

In yet another embodiment the implant further comprises a therapeutic to aid in retinal re-attachment. Such drug can be coated onto the implant, or where the implant is a polymer, incorporated into the structure via means known in the art, i.e., into an area with a surface treatment specifically intended to capture and release drug in a preferred manner or loaded into a reservoir incorporated into the device. Preferably, the device comprises biocompatible metals, metal alloys, biocompatible polymers or possibly combinations thereof. For example, a type of biocompatible polymer usable with the device according to the present invention includes the resilient polymeric materials disclosed in international publication WO 91/12779. Additional biocompatible metals and alloys include those disclosed, e.g., in U.S. Pat. Nos. 4,733,665; 4,800,882; 4,886,062; and 6,478,815, the contents of which are expressly incorporated herein by reference. Such metals and alloys include, but are not limited to, silver, tantalum, stainless steel, annealed steel, gold, copper alloys, cobalt alloys (e.g., cobalt-chromium-nickel alloys), titanium, tungsten, zirconium, niobium, iridium, and platinum. Shaped-memory metal alloys (e.g., Nitinol, a super elastic titanium alloy) can also be used to form the devices discussed herein.

Biocompatible polymers for use with the device of the present invention can be non-bioabsorbable, bioabsorbable in part, or substantially completely bioabsorbable. The stable, non-bioabsorbable polymers that may be used for device construction are those generally exhibiting a low chronic tissue response (including: irritation, adherence, inflammation, etc). These include polyesters, polyamides, polyolefins (substituted or unsubstituted with e.g., halides), polyurethanes (e.g., polyurethane urea, segmented polyurethane urea/heparin) and silicones (e.g., siliconeA, siliconeB, and silicone C).

In the event the implant must be manufactured from a material which is not biocompatible, the use of biocompatible coatings can render the implant biocompatible. Biocompatible surfaces are important for medical devices. The term 'biocompatible' is used herein to mean a surface which causes either no or a minimal reaction when it comes into contact with a human or animal body or its blood, fluids or other biological membranes. Examples of biocompatible coatings are well known in the art and include, PTFE, hydroxyapatite and silicone . One of skill in the art will based on the materials in the implant know which coating are suitable. U.S. Pat. No. 6,406,792 teaches the use of coatings made by reacting a reactive polysiloxane. U.S. Pat. No. 3,574,673 teaches the use of organosiloxane polymers which can be cured on various surfaces such as needles to provide a lubricating film. Similarly, U.S. Pat. No. 4,720,521 teaches coating devices such as needles or catheters with a curable silicone composition to form a crosslinked, adherent coating which serves as a matrix for a non-reactive lubricating silicone polymer. U.S. Pat. No. 5,061,738 also teaches a blood compatible, lubricious composition for use on medical articles. The contents of the above patents are incorporated by reference, and are not considered limiting in choosing biocompatible coatings.

Polyesters include e.g., polyethylene terephthalate (PET) and polybutylene terephthalate (PBT). Other polyesters include polyethylene terephthalate copolymers or polybutylene terephthalate copolymers using, as comonomers, saturated dibasic acids such as phthalic acid, isophthalic acid, sebacic acid, adipic acid, azelaic acid, glutaric acid, succinic acid, and oxalic acid; polyethylene terephthalate copolymers or polybutylene terephthalate copolymers using, as diol comonomers, 1,4-cyclohexanedimethanol, diethylene glycol, and propylene glycol; and blends thereof. Specific examples of these polyethylene terephthalate copolymers include polyethylene terephthalate/isophthalate (PET/I), polyethylene terephthalate/sebacate (PET/S), and polyethylene terephthalate/adipate (PET/A). Specific examples of the polybutylene terephthalate polymers include polybutylene terephthalate (PBT), polybutylene terephthalate/isophthalate (PBT/I), polybutylene terephthalate/sebacate (PBT/S), polybutylene terephthalate/adipate (PBT/A), polybutylene/ethylene terephthalate, and polybutylene/ethylene terephthalate/isophthalate. Also usable are polyesters that are copolymerized or modified with other third components in order to improve their physical characteristics. The polyester resins may be stretched either monoaxially or biaxially.

Polyamides include, e.g., polyamides, Nylon 66, poly-caprolactam, and molecules of the form —NH—$(CH_2)_n$—CO— and NH—$(CH_2)_x$—NH—CO—$(CH_2)_y$—CO, wherein n is preferably an integer in from about 6 to about 13, x is an integer from about 6 to about 12, and y is an integer from about 4 to about 16.

Polyolefins include, e.g., polypropylene, polyethylene, polyisobutylene, polytetrafluoroethylene, expanded polytetrafluoroethylene, ethylene-alphaolefin copolymers. Polyolefins also include copolymers of olefins and unsaturated glycidyl group-containing monomers, and terpolymers or multipolymers of olefins, unsaturated glycidyl group-containing monomers and ethylenically unsaturated monomers. Examples of olefins include propylene, butene-1, hexene-1, decene-1, octene-1. Examples of the unsaturated glycidyl group-containing monomers include e.g., glycidyl esters such as glycidyl acrylate, glycidyl methacrylate, monoglycidyl itaconate, monoglycidyl butenetricarboxylate, diglycidyl butenetricarboxylate, and triglycidyl butenetricarboxylate; glycidyl esters of .alpha.-chloroallyl, maleic acid, crotonic acid, and fumaric acid; glycidyl ethers such as vinyl glycidyl ether, allyl glycidyl ether, 2-methyallyl glycidyl ether, glycidyloxyethyl vinyl ether, and styrene-p-glycidyl ether; and p-glycidylstyrene. In addition to olefins, other ethylenically unsaturated monomers of the invention may also be used to form homo- or copolymers. Such monomers include, e.g., vinyl esters and .alpha.- and .beta.-ethylenically unsaturated carboxylic acids and derivatives thereof. Examples include vinyl esters such as vinyl acetate; vinyl propionate; vinyl benzoate; acrylic acid; methacrylic acid and esters thereof, such as methyl, ethyl, propyl, butyl, 2-ethylhexyl, cyclohexyl, dodecyl, and octadecyl acrylates or methacrylates; maleic acid; maleic anhydride; itaconic acid; fumaric acid; maleic mono and diesters; vinyl chloride; vinyl ethers such as vinyl methyl ether and vinyl ethyl ether; and acrylic amides.

Other useful nonbioabsorbable polymers include polyacrylamides, poly(meth)acrylates, polyalkyl oxides (polyethylene oxide), polyvinyl alcohol homo- and copolymers (e.g., PVA foams, polyethylene vinyl alcohol), polyethylene glycol homo- and copolymers, polylysine, polyoxamers, polysiloxanes (e.g., polydimethylsiloxane), polyethyloxazoline, and polyvinyl pyrrolidone, as well as hydrogels such as those formed from crosslinked polyvinyl pyrrolidinone and polyesters (e.g., polyvinyl pyrrolidone/cellulose esters and polyvinyl pyrrolidone/poly urethane) Further nonbioabsorbable polymeric materials include acrylic polymers (e.g., methacrylate) and copolymers, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polymethylidene maleate, polyacrylonitrile, polyvinyl ketones, polyvinyl aromatics (e.g., polystyrene), polyvinyl esters (e.g., polyvinyl acetate), copolymers of vinyl monomers with each other and olefins (e.g., etheylene-methyl methacrylate copolymers, acrylonitrile-styrene copolymers, ABS resins and ethylene-vinyl acetate copolymers), alkyd resins, polycarbonates, polyoxymethylenes, polyimides, polyethers, epoxy resins, rayon, rayon-triacetate, cellulose, cellulose acetate, cellulose acetate butyrate, cellophane, cellulose nitrate, cellulose propionate, cellulose ethers (e.g., carboxymethyl cellulose and hydoxyalkyl celluloses), cellulose esters, and combinations thereof.

Preferred materials include those useful for manufacturing contact lenses including silicone elastomers, silicone-containing macromers including, without limitation, those disclosed in U.S. Pat. Nos. 5,371,147, 5,314,960, and 5,057,578 incorporated in their entireties herein by reference, hydrogels, silicone-containing hydrogels, and the like and combinations thereof. In some embodiments the lens material may contain a siloxane functionality, including, without limitation, polydimethyl siloxane macromers, methacryloxypropyl polyalkyl siloxanes, and mixtures thereof, a silicone hydrogel or a hydrogel, made of monomers containing hydroxy groups, carboxyl groups, or combinations thereof. Materials for making soft contact lenses are well known and commercially available and include acquafilcon, etafilcon, genfilcon, lenefilcon, balafilcon, lotrafilcon, or galyfilcon.

Bioabsorbable polymers may also be used for the manufacture of the present invention. Bioabsorbable polymers are advantageous in that the device or portions thereof formed from these materials can be absorbed into the body and therefore do not require physical removal. Bioabsorbable polymers include, for example, those found in Tanquay et al. (Contemp. Intervention. Tech. 12(4):699-713, (1994)). Bioabsorbable polymers differ from nonbioabsorbable polymers in that they can be degraded into substantially non-toxic biodegradation products, while used in in vivo therapy. Degradation generally involves breaking down the polymer into its monomeric subunits. For example, the ultimate hydrolytic breakdown products of a poly(phosphonate) are phosphonate, alcohol, and diol, all of which are potentially non-toxic. The rate of degradation of bioabsorbable polymers is related to various polymer properties, such as permeability, water solubility, crystallinity, and physical dimensions.

Bioabsorbable polymers include various types of aliphatic polyesters, polyorthoesters, polyphosphazenes, poly(amino acids), copoly(ether-esters), polyalkylene oxalates, polyamides, poly(iminocarbonates), polyoxaesters, polyamidoesters, polyoxaesters containing amido groups, poly(anhydrides), poly(hydroxybutyrates), poly(phosphate-esters), polyurethanes, polyanhydrides, biomolecules, and blends thereof.

Bioabsorbable polyesters may be used and are described, e.g., in Pitt et al., "Biodegradable Drug Delivery Systems Based on Alipathic Polyesters: Application to Contraceptives and Narcotic Antagonists", Controlled Release of Bioactive Materials, 19-44 Richard Baker ed., (1980). Aliphatic polyesters include homopolymers and copolymers of lactides (including lactic acid and D-, L-, and meso lactide), .epsilon.-caprolactone, glycolide (including glycolic acid and lactide/glycolide copolymers), hydroxybutyrate, hydroxyvalerate, dioxanone (e.g., para-dioxanone), trimethylene carbonate (and its alkyl derivatives), 1,4-dioxepan-2-one, 1,5-dioxepan-2-one, 6,6-dimethyl-1,4-dioxan-2-one, and polymer blends thereof. Bioabsorbable polyorthoesters may also be used and are described e.g., by Heller et al., "Release of Norethindrone from Poly(ortho Esters)", Polymer Engineering Sci., 21:11, 727-31 (1981) and also by Heller in Handbook of Biodegradable Polymers, edited by Domb, Kost and Wisemen, Hardwood Academic Press (1997) p. 99-118. Polyorthoesters include, e.g., polyglycolic acid and polylactic acid such as poly-L-lactic acid (PLLA); poly D,L-lactic acid; and poly-D-lactic acid. Bioabsorbable polyphosphazenes are described, e.g., by Dunn et al., in U.S. Pat. Nos. 5,340,849; 5,324,519; 5,278,202; and 5,278,201. Polyphosphazenes, co-, ter- and higher order mixed monomer based polymers made from L-lactide, D,L-lactide, lactic acid, glycolide, glycolic acid, para-dioxanone, trimethylene carbonate and .epsilon.-caprolactone, are described by Allcock in The Encyclopedia of Polymer Science, Vol. 13, p. 31-41, Wiley Intersciences, John Wiley & Sons (1988) and by Vandorpe, Schacht, Dejardin and Lemmouchi in the Handbook of Biodegradable Polymers, edited by Domb, Kost and Wisemen, Hardwood Academic Press (1997), p. 161-182. Poly(amino acids) and pseudo-poly(amino acids) are described, e.g., by Pulapura et al., "Trends in the Development of Bioresorbable Polymers for Medical Applications," J. of Biomaterials Appl., 6:1, 216-50 (1992); Poly(iminocarbonate) is described, e.g., in Kemnitzer and Kohn, Handbook of Biodegradable Polymers, edited by Domb, Kost and Wisemen, Hardwood Academic Press (1997), p. 251-272. Copoly(ether-esters) include, e.g., PEO/PLA and others described by Cohn and Younes, Journal of Biomaterials Research, Vol. 22 (1998), p. 993-1009, and by Cohn, Polymer Preprints (ACS Division of Polymer Chemistry) Vol. 30(1), (1989) p. 498. Polyalkylene oxalates include those described in U.S. Pat. Nos. 4,208,511; 4,141,087; 4,130,639; 4,140,678; 4,105,034; and 4,205,399. Polyanhydrides include those resulting from the polymerization of diacids of the form HOOC—$C_6H_4$—O—$(CH_2)_m$—O—$C_6H_4$—COOH where m is an integer from about 2 to about 8 and also include copolymers resulting from the copolymerization of these diacids with aliphatic alpha-omega diacids of up to 12 carbons. As is known in the art, the monomer ratios in polyanhydride copolymers may be varied so that the resulting copolymer is surface eroding. Polyoxaesters, polyoxaamides, and polyoxaesters containing amines and/or amido groups are described in one or more of U.S. Pat. Nos. 5,464,929; 5,595,751; 5,597,579; 5,607,687; 5,618,552; 5,620,698; 5,645,850; 5,648,088; 5,698,213 and 5,700,583. Bioabsorbable poly(phosphate-esters), e.g., poly(phosphates), poly(phosphonates) and poly(phosphites), are described, e.g., by Penczek et al., Handbook of Polymer Synthesis, Chapter 17: "Phosphorus-Containing Polymers", p. 1077-1132 (Hans R. Kricheldorf ed., 1992) and in U.S. Pat. No. 6,153,212. Bioabsorbable polyurethanes are described, e.g., by Bruin et al., "Biodegradable Lysine Diisocyanate-based Poly-(Glycolide-co-.epsi-lon.-Caprolactone)-Urethane Network in Artificial Skin", Biomaterials, 11:4, 291-95 (1990). Bioabsorbable polyanhydrides are described, e.g., by Leong et al., "Polyanhydrides for Controlled Release of Bioactive Agents", Biomaterials, 7:5, 364-71 (1986).

Polymeric biomolecules may also advantageously be used with the device or portions of the device according to the present invention. Polymeric biomolecules include naturally occurring materials that may be enzymatically degraded in the human body or those that are hydrolytically unstable in the human body. Such materials include albumin, alginate, gelatin, acacia, cellulose dextran, ficoll, hydroxyethyl cellulose, hydroxypropyl cellulose, hydroxypropylmethyl cellulose, carboxyethyl cellulose, carboxymethyl cellulose, fibrin, fibrinogen, collagen, elastin, dextran sulfate and absorbable biocompatable polysaccharides such as chitosan, deacetylated chitosan, starch, fatty acids (and esters thereof), glucoso-glycans and hyaluronic acid.

Other useful materials include bioabsorbable elastomers, preferably aliphatic polyester elastomers. In the proper proportions aliphatic polyester copolymers are elastomers. If used as coating materials, elastomers advantageously adhere well to the metal portions of the device and can withstand significant deformation without cracking. Examples of suitable bioabsorbable elastomers are described in U.S. Pat. No. 5,468,253. Preferred bioabsorbable biocompatible elastomers are based on aliphatic polyesters, including elastomeric copolymers of $\epsilon$.-caprolactone and glycolide (preferably having a mole ratio of $\epsilon$-caprolactone to glycolide from about 35:65 to about 65:35); elastomeric copolymers of .epsilon.-caprolactone and lactide, including L-lactide, D-lactide and blends thereof or lactic acid copolymers (preferably having a mole ratio of .epsilon.-caprolactone to lactide from about 35:65 to about 90:10); elastomeric copolymers of p-dioxanone (1,4-dioxan-2-one) and lactide including L-lactide, D-lactide and lactic acid (preferably having a mole ratio of p-dioxanone to lactide from about 40:60 to about 60:40); elastomeric copolymers of .epsilon.-caprolactone and p-dioxanone (preferably having a mole ratio of .epsilon.-caprolactone to p-dioxanone from about 30:70 to about 70:30); elastomeric copolymers of p-dioxanone and trimethylene carbonate (preferably having a mole ratio of p-dioxanone to trimethylene carbonate from about 30:70 to about 70:30); elastomeric copolymers of trimethylene carbonate and glycolide (preferably having a mole ratio of trimethylene carbonate to glycolide from about 30:70 to about 70:30); elastomeric copolymers of trimethylene carbonate and lactide including L-lactide, D-lactide, and blends thereof; or lactic acid copolymers (preferably having a mole ratio of trimethylene carbonate to lactide from about 30:70 to about 70:30) and blends thereof.

The present invention also includes introducing an agent into a body using one of the above-discussed device. In a preferred embodiment, the agent(s) is carried by one or more of the strands of the device and released within the body over a predetermined period of time. Local delivery of an agent is advantageous in that its effective local concentration is much higher when delivered by the device than that normally achieved by systemic administration. The rail elements 12, 12', 120 and 312, which are relatively inelastic in their transverse strength properties, may carry one or more of the above-referenced agents for applying to a vessel as the vessel moves into contact with the agent carrying elements after deployment of the device within the eye. Drug delivery may also be achieved via other embodiments such as impregnated polymers, surface treatments of metals and polymers, polymers with reservoirs, etc.

The above-discussed device can deliver one or more known agents, including therapeutic and pharmaceutical agents, such as a drug, at a site of contact with a portion of the eye or when released from a carrier as is known. This release can be a timed release, release to a certain area of the retinal tissue bed, release generally to the eye or other arrangements as necessary. These agents can include any known therapeutic drugs, antiplatelet agents, anticoagulant agents, antimicrobial agents, antimetabolic agents and proteins used for the treatment, prevention, diagnosis, cure, or mitigation of disease or illness; substances that affect the structure of function of the body; and prodrugs, which become biologically active or more active after placement in a given physiological environment. Agents may include medicaments, vitamins, mineral supplements. The agents may also include any of those disclosed in U.S. Pat. No. 6,153,252 to Hossainy et al. and U.S. Pat. No. 5,833,651 to Donovan et al., both of which are hereby incorporated by reference in their entirety.

Preferred agents usable with the implantable device disclosed herein are those that inhibit growth of tissue through any of a variety of approaches and include anti-inflammatory immuno-modulators including dexamethasone, m-prednisolone, interferon .gamma.-lb, leflunomide, sirolimus, everolimus, tacrolimus, mycophenolic acid, mizoribine, cyclosporine, rapamycin, and tranilast; antiproliferatives including QP-2, taxol, actinomycine, methotrexate, angiopeptin, vincristine, mitomycin, statins, CMYC antisense, ABT-578, RestenASE, 2-chlorodeoxyadenosine, PCNA ribozyme, paclitaxel, rapamycin, everolimus and tacrolimus; migration inhbitors/ECM-modulators including batimastat, prolylhydroxylase inhibitors, halofuginone, C-proteinase inhibitors, probucol, rapamycin, everolimus and tacrolimus; and agents that promote healing and reendothelialization including BCP671, VEGF, and estrogen. Additional agents, such as those discussed below, can also be used.

Non-limiting examples of agents include those within the following therapeutic categories: analgesics, such as non-steroidal anti-inflammatories (NSAIDs), steroidal anti-inflammatories, COX 2 selective inhibitors, opiate agonists and salicylates; angiogenesis inhibitors; antiasthmatics; antihistamines/antipruritics, such as $H_1$-blockers and $H_2$-blockers; anti-infectives, such as anthelmintics, anti-anaerobics, antibiotics, aminoglycoside antibiotics, antifungal antibiotics, macrolide antibiotics, miscellaneous .beta.-lactam antibiotics, penicillin antibiotics, quinolone antibiotics, sulfonamide antibiotics, tetracycline antibiotics, antimicrobials, antibacterials, antimycobacterials, antituberculosis antimycobacterials, antiprotozoals, antimalarial antiprotozoals, antiviral agents, anti-retroviral agents, scabicides, and urinary anti-infectives; antiarthritics; antifibrinolytics; antineoplastics, such as alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; calcium regulators; autonomic agents, such as anticholinergics, xanthines, mast cell stabilizers, antimuscarinic anticholinergics, ergot alkaloids, parasympathomimetics, cholinergic agonist parasympathomimetics, cholinesterase inhibitor parasympathomimetics, sympatholytics, .alpha.-blocker sympatholytics, .beta.-blocker sympatholytics, sympathomimetics, and adrenergic agonist sympathomimetics; cardiovascular agents, such as antianginals, .beta.-blocker antianginals, calcium-channel blocker antianginals, nitrate antianginals, antiarrhythmics, cardiac glycoside antiarrhythmics, class I, II, III, or IV antiarrhythmics, antihypertensive agents, .alpha.-blocker antihypertensives, angiotensin-converting enzyme inhibitor (ACE inhibitor) antihypertensives, .beta.-blocker antihypertensives, calcium-channel blocker antihypertensives, central-acting adrenergic antihypertensives, diuretic anti-hypertensive agents, peripheral vasodilator anti-hypertensives, anti-lipidemics, inotropes, cardiac glycoside inotropes, and thrombolytics/fibrinolytics; dermatological agents, such as antihistamines, anti-inflammatory agents, corticosteroid anti-inflammatory agents, and antipruritics/local anesthetics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as anti-diarrheals, antiemetics/antinauseants, gastrointestinal anti-inflammatory agents, salicylate gastrointestinal anti-inflammatory agents, anti-ulcer/anti-reflux agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; enzyme inhibitors; general anesthetics, such as halogenated anesthetics, barbiturate anesthetics, benzodiazepine anesthetics, and opiate agonist anesthetics; hematological agents, such as antianemia agents, hematopoietic antianemia agents, coagulation agents, anticoagulants, hemorheologic agents, hemostatic coagulation agents, antiplatelet agents, thrombolytic enzyme coagulation agents, and plasma volume expanders; hormones, hormone modifiers, and thyroid hormones, such as abortifacients, adrenal agents, adrenal corticosteroids, androgens, anti-androgens, antidiabetics, sulfonylurea antidiabetic agents, antihypoglycemic agents, progestins, estrogens, fertility agents, oxytocics, parathyroid agents, pituitary hormones, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, immunosuppressive anti-inflammatory agents, salicylate anti-inflammatory agents, skeletal muscle relaxants, neuromuscular blocker skeletal muscle relaxants, and reverse neuromuscular blocker skeletal muscle relaxants; anti-apoptotics; neurological agents, such as anticonvulsants, barbiturate anticonvulsants, benzo-diazepine anticonvulsants, anti-migraine agents, anti-parkinsonian agents, anti-vertigo agents, opiate agonists, and opiate antagonists; ophthalmic agents, such as anti-glaucoma agents, .beta.-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic agents, ophthalmic corticosteroid anti-inflammatory agents, and ophthalmic nonsteroidal anti-inflammatory drugs; psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; vitamins, such as vitamin A, vitamin B, vitamin C, vitamin D, vitamin E, and vitamin K; amino acids; and proteins, such as antibodies (e.g., monoclonal antibodies, polyclonal antibodies, and antibody fragments).

The following are examples of agents within the various therapeutic categories discussed above that can be used alone or with another one or more of these agents or specifically formulated to deliver optimal therapeutic effect in one or more of the device embodiments:

Analgesics include, e.g., para-aminophenol derivatives (e.g., acetaminophen), indole and indene acetic acids (e.g., etodalac), heteroaryl acetic acids (e.g., diclofenac and ketorolac), arylpropionic acids (e.g., ibuprofen), anthranilic acids (e.g., mefenamic acid and meclofenamic acid), enolic acids (e.g., tenoxicam and oxyphenthatrazone), nabumetone, gold compounds (e.g., gold sodium thiomalate), buprenorphine, propoxyphene hydrochloride, propoxyphene napsylate, meperidine hydrochloride, hydromorphone hydrochloride, morphine, oxycodone, codeine, dihydrocodeine bitartrate. pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, methotrimeprazine, cinnamedrine hydrochloride, meprobamate, ketoprofen, flurbiprofen, naproxen, ramifenazone, meloxicam, fluazacort, celecoxib, rofecoxib, valdecoxib, nepafenac, ISV-205; angiogenesis inhibitors include, e.g., angiostatin (plasminogen fragment), vascular endothelial cell growth factor (VEGF), fibroblast growth factor (FGF), nitric oxide donors, antiangiogenic anithrombin III, cartilage-derived inhibitor (CD1), CD59 complement fragment, endostatin (collagen XVIII fragment), fibronectin fragment, gro-beta, heparinases, heparin hexasaccharide fragment, human chorionic gonadotropin (hCG), .alpha.-, .beta.-, and .gamma.-interferon, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF-4), prolactin 16 kD fragment, proliferin-related protein (PRP), retinoids, tetrahydrocortisol-S, thrombospondin-1 (TSP-1), transforming growth factor-beta (TGF-b), vasculostatin, vasostatin (calreticulin fragment), apolipoprotein E, TBC-2576; antiasthmatics include, e.g., ketotifen and traxanox; antidepressants include, e.g., nefopam, oxypertine, amoxapine, trazodone, maprotiline, phenelzine, desipramine, nortriptyline, tranylcypromine, fluoxetine, doxepin, imipramine, imipramine pamoate, isocarboxazid, trimipramine, and protriptyline; antidiabetics include, e.g., biguanides (e.g., metformin), sulfonylurea derivatives (e.g., tolbutamide, chlorpropamide, acetohexamide, tolazamide, and glimepiride), .alpha.-glucosidase inhibitors (e.g., acarbose), thiazolidinediones (e.g., troglitazone), and metglinide analogs (e.g., repaglinide); antihypertensive agents include, e.g., propanolol, propafenone, oxyprenolol, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine; antineoplastics include, e.g., cladribine (2-chlorodeoxyadenosine), nitrogen mustards (e.g., cyclophosphamide, mechlorethamine, melphalan, and chlorambucil), ethylenimines and methylmelamines (e.g., hexamethylmelamine and thiotepa), alkyl sulfonates (e.g., busulfan), nitrosoureas (e.g., streptozocin, carmustine (BCNU), methyl-CCNU and analogs), trazenes (e.g., dacarbazinine (DTIC)), platinum coordination complexes (e.g., carboplatin and cisplatin), procarbazine, hydroxyurea, mitotane, am inoglutethimide, camptothecin phenesterine, paclitaxel, docetaxel, vinca alkaloids (e.g., vinblastine, vincristine, and vinorelbine), epidipodophyllotoxins (e.g., etoposide (VP-16) and teniposide), tamoxifen, and piposulfan; anxiolytics include, e.g., lorazepam, buspirone, prazepam, chlordiazepoxide, oxazepam, clorazepate dipotassium, hydroxyzine pamoate, hydroxyzine hydrochloride, alprazolam, droperidol, halazepam, chlormezanone, and dantrolene; enzyme inhibitors include, e.g., selegiline or its hydrochloride salt, lazabemide, rasagiline, moclobemide, entacapone, tolcapone, nitecapone, Ro 40-7592, clozapine, risperidone, olanzapine, and quetiapine; immunosuppressives include, e.g., calcineurin inhibitors (e.g., cyclosporine and tacrolimus (FK-506)), antiproliferative/antimetabolic agents (e.g., sirolimus, QP-2, taxol, actinomycin, dactinomycin, daunorubicin, angiopeptin, mitomycine, bleomycin, doxorubicin, epirubicin, mitomycin, idarubicin, anthracyclines, mitoxantrone, plicamycin, CMYC antisense, ABT-578, RestenASE, 2-chloro deoxyadenosine, PCNA ribozyme, rapamycin, folic acid analogs (e.g., methotrexate), fluorouracil (5-FU), floxuridine, cytarabine, mercaptopurine, thioguanine, pentostatin, cyclophosphamide, thalidomide, chorambucil, leflunomide, batimastat, and mizoribine), everolimus, azathioprine, cytoxan, mycophenolic acid, mycophenolate mofetil, and tranilast; antimigraine agents include, e.g., ergotamine, isometheptene mucate, and dichloralphenazone; sedatives and hypnotics include, e.g., barbiturates (e.g., pentobarbital and secobarbital), flurazepam hydrochloride, triazolam, and midazolam; calcium-channel blocker antianginals include, e.g., nifedipine and diltiazem; nitrate antianginals include, e.g., nitroglycerin, isosorbide dinitrate, pentaerythritol tetranitrate, and erythrityl tetranitrate; antipsychotics include, e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine; antimanics include, e.g., lithium carbonate; antiarrhythmics include, e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine; antiarthritics include, e.g., phenylbutazone, sulindac, penicillanine, salsalate, piroxicam, indomethacin, meclofenamate. ketoprofen, auranofin, aurothioglucose, tolmetin, and tolmetin sodium; anti-gout agents include, e.g., colchicine and allopurinol; anticoagulants include e.g., danaparoid, lepirudin, dicumarol, acenocoumarol, heparin, heparin salts (e.g., heparin sodium), warfarin sodium, 4-hydroxycoumarin, phenprocoumon, indan-1,3 dione, anisindione, warfarin sodium, tissue factor pathway inhibitor (TFPI), tifacogin, ancrod, bromindione, clorindione, coumetarol, cyclocoumarol, 4-coumarinol, desirudin, dexran sodium sulfate, diphenadione, ethyl biscoumacetate, fluindione, hirudin, nadroparin calcium, nafamostat mesylate, oxazidione, phenindione, phosvitin, picotamide, sodium apolate, thrombocid, tioclomarol, warfarin, aprosulate sodium, ART 123, bivalirudin, BMS 189090, BMS 186282, BMS 189664, BMS 191032, corsevin M, CS 747, curdlan sulfate, DPC 423, DX 9065a, efegatran, fondaparinux sodium, GR 144053, inogatran, LB 30057, melagatran, MR 33, napsagatran, NSL 9403, SR 90107, YM 75466, ZK 805412, ZK 807834, OGS 15435, JTV 803, LY 287045, P 8720, RE 1492, Ro 43-8857, S 18326, S 31214, SK 549, SB 249417, SR 123781A, and UK 156406; thrombolytics/fibrinolytics include, e.g., urokinase, streptokinase, alteplase, phosphorylcholine, plasmin, plasminogen, angiokinase, anistreplase, prourokinase, reteplase, saruplase, tissue plasminogen activator, actinokinase, .alpha.2-antiplasmin, antithrombin, E 6010, fibrolase, lys-plasminogen, lanoteplase, lumbrokinase, metalloproteinase, monteplase, PAI proteinase inhibitor, pamiteplase, staphylokinase, and tenecteplase; antifibrinolytics include, e.g., aminocaproic acid; hemorheologic agents include, e.g., pentoxifylline; antiplatelet agents include, e.g., aspirin, ticlopidine, abciximab, clopidogrel, eptifibatide, tirofiban, and glycoprotein IIb/IIa inhibitors, argatroban, cilostazole, cloricromene, dalteparin, daltroban, defibrotide, dipyridamole, enoxaparin, iloprost, indobufen, isbogrel, lamifiban, lotrifiban nadroparin calcium, orbofiban, pamicogrel KBT 3022, plafibride, picotamide, ozagrel, ramatroban, reviparin sodium, ridogrel, roxifiban, satigrel, sibrafiban, sulotroban, taprostene, ticlopidine, triflusal, amrinone, cilostamide, dialzep, enoximone, milrinone, naftazone, pimilprost, pimobendan, sarpogrelate, sulfinpyrazone, vapiprost, vesnarinone, xemilofiban, zaprinast, zeria Z 335, A 02131-1, camonagrel, cangrelor, DMP 728, DMP 802, elarofiban, EMD 122347 FK 633, FXV 673, ifetroban, L 734217, lefradafiban, MK 852, ON 579, R 99224, RGD 039, RGD 891, RPR 109891, Ro 48-3657, Ro 44-3888, S 1197, SDZ-GPI 562, SL 650472, SM 20302, SR 121566A, SR 121787A, TA 993, TAK 029, XV 454, XV 459, YC-1, aspalatone, BAY 41-2272, BM 531, BM 14515, C 186-65, CS 570, FR 158999, fradafiban, L 750034, linotroban, ME 3277, MED 27, NQ 12, NQ 301, NQ 304, NSL 9511, NSP 513, 4-pentynoic acid, 3-[[4-[[4-(aminomethyl)-phenyl]amino-]-1,4-dioxobutyl]amino]-ethyl ester, RE 2047, SCH 79797, SM 10906, SR 25989, TP 9201, XJ 735, XR 300, XU 057, XU 063, XU 065, Y 909, ZD 2486, and ZD 9583; anti-apoptotics include, e.g., CGP 3466, CEP-1347/KT-7515, TCH-346, and WHI-P131; neurological agents include, e.g., timolol, dapiprazole, levobunolol, betaxolol, befunolol, carteolol, metipranolol, AMO-140, bunazosin, adaprolol, ISV-208, L-653328, cetamolol, H-216/44, KRG-332, levobetaxolol, metazosin, NCX-904, NCX-905, guanethidine, brimonidine, apraclonidine, AGN-195795, AGN-191103, AGN-190532, AGN-192172, AGN-193080, AGN-190837, talipexole, thiourea, dipivefrin, epinephrine, phenylephrine, cocaine, hydroxyamphetamine, naphazoline, tetrahydrozoline, levodopa, levodopa/carbidopa, levodopa/benserazide, amantadine, sumanirole, pergolide, pramipexole, ropinirole, bromocriptine, lisuride or 9, 10 dihydrolisuride, apomorphine or N-propylnoraporphine, N-propyl noraporphine, PHNO, N-0437 (racemate) and N-9023 (purified negative enantiomer), cabergoline, ciladopa, ABT-431, lergotrile, DIB1508Y, and ABT418m; selective serotonin re-uptake inhibitors (SSRIs) include, e.g., paroxetine, and serataline; anticonvulsants include, e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione; anti-parkinsonian agents include, e.g., ethosuximide; antihistamines/antipruritics include, e.g., hydroxyzine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine; calcium regulators include, e.g., calcitonin and parathyroid hormone; antibacterials include, e.g., amikacin sulfate, aztreonam, chloramphenicol, chloramphenicol palirtate, clindamycin, clindamyc in palmitate, clindamycin phosphate, metronidazole, gentamicin sulfate, lincomycin hydrochloride, tobramycin sulfate, vancomycin hydrochloride, polymyxin B sulfate, colistimethate sodium, and colistin sulfate; antibiotics include, e.g., neomycin, streptomycin, chloramphenicol, cephalosporin, ampicillin, penicillin, tetracycline, and ciprofloxacin; antifungal antibiotics include, e.g., griseofulvin, ketoconazole, itraconizole, amphotericin B, nystatin, and candicidin; antiviral agents include, e.g., zidovudine (AZT), amantadine hydrochloride, ribavirin, and acyclovir; antimicrobials include, e.g., cephalosporins (e.g., cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, cefadroxil, and cefuroxime sodium), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium), and erythromycins (e.g., erythromycin ethylsuccinate, erythromycin, erythromycin estolate, erythromycin lactobionate, erythromycin stearate, and erythromycin ethylsuccinate), and tetracyclines (e.g., tetracycline hydrochloride, doxycycline hyclate, minocycline hydrochloride, azithromycin, and clarithromycin); anti-infectives include, e.g., GM-CSF; sympathomimetics include, e.g., epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, epinephrine, and epinephrine bitartrate; anticholinergics include, e.g., ipratropium bromide, benzhexol, trihexphenidyl, benzotropine, diphenhydramine hydrochloride, orphenadrine, chlorphenoxamine, amitriptyline, doxepin, imipramine, nortriptyline, biperiden, ethopropazine, procyclidine, cycrimine, and ethopropzaine; xanthines include, e.g., aminophylline, dyphylline, metaproterenol sulfate, and aminophylline; mast cell stabilizers include, e.g., cromolyn sodium; bronchodilators include, e.g., salbutamol, budesonide, ketotifen, salmeterol, xinafoate, terbutaline sulfate, theophylline, nedocromil sodium, metaproterenol sulfate, flunisolide, and fluticasone proprionate; androgens include, e.g., danazol, testosterone cypionate, fluoxymesterone, ethyltestosterone, testosterone enathate, methyltestosterone; estrogens include, e.g., estradiol, estropipate, and conjugated estrogens; progestins include, e.g., methoxyprogesterone acetate, and norethindrone acetate; adrenal corticosteroids include, e.g., cortisol, cortisone, oxandrolone, creatine, erythropeotin, dehydroepiandrosterone triamcinolone, betamethasone, betamethasone sodium phosphate, dexamethasone, dexamethasone sodium phosphate, dexamethasone acetate, prednisone, prednisolone, methylprednisolone acetate suspension, triamcinolone acetonide, hydrocortisone sodium succinate, triamcinolone hexacetonide, hydrocortisone, hydrocortisone cypionate, fludrocortisone acetate, paramethasone acetate, prednisolone tebutate, and prednisolone acetate; thyroid hormones include, e.g., levothyroxine sodium; antihypoglycemic agents include, e.g., human insulin, purified beef insulin, purified pork insulin, glyburide, chlorpropamide, glipizide, tolbutamide, and tolazamide; anti-lipidemics include e.g., antiatherosclerotics and antihypercholesteremics (e.g., cholesteryl ester transfer protein (CETP) inhibitors, such as those disclosed in U.S. Pat. No. 6,458,850; ileal bile acid transport (IBAT) inhibitors, such as those disclosed in U.S. Pat. No. 6,458,851; and HMG CoA reductase inhibitors, such as those disclosed in U.S. Pat. No. 6,462,091), fibric acid derivatives (e.g., clofibrate, fenofibrate, ciprofibrate, benzafibrate, clinofibrate, binifibrate and gemfibrozil), and nicotinic acid derivatives (e.g., nicotinic acid, niceritrol, and acipimox), dextrothyroxine sodium, probucol, pravastatin, atorvastatin, lovastatin, and niacin; antiulcer/antireflux agents include, e.g., famotidine, cimetidine, and ranitidine hydrochloride; antiemetics/antinauseants include, e.g., meclizine hydrochloride, nabilone, prochlorperazine, dimenhydrinate, promethazine hydrochloride, thiethylperazine, and scopolamine; collagen synthesis inhibitors include, e.g., prolyl hydroxylase inhibitors, C-proteinase inhibitors, and halofuginone; vitamins include oil-soluble vitamins (e.g., vitamins A, D, E, and K); amino acids include, e.g., valine, leucine, and isoleucine; proteins include, e.g., cyclophilin, antithymocyte globulin, immunoglobulin, muromonab-CD3, daclizumab, basiliximab, infliximab, etanercept, DNase, alginase, L-asparaginase, superoxide dismutase (SOD), lipase, metallothionine, a polipoprotein E, oxandrolone, creatine, dehydro epiandrosterone, platelet derived growth factor, fibrin, fibrinogen, collagen, interleukins 1 through 18, luteinizing hormone releasing hormone (LHRH), gonadotropin releasing hormone (GnRH), and transforming growth factor-.beta. (TGF-.beta.), tumor necrosis factor-.alpha. and .beta. (TNF-.alpha. and .beta.), nerve growth factor (NGF), growth hormone releasing factor (GHRF), epidermal growth factor (EGF), fibroblast growth factor homologous factor (FG-FHF); hepatocyte growth factor (HGF); insulin growth factor (IGF), invasion inhibiting factor-2 (IIF-2), bone morphogenetic proteins 1-7 (BMP 1-7), somatostatin; thymosin-.alpha.-1, and .gamma.-globulin. Various biologically active forms of these proteins, including recombinant forms, mutants, complements, analogs, derivatives, and fragments are also contemplated. Other useful agents include nucleic acids (e.g., sense or anti-sense nucleic acids encoding any therapeutically useful protein, including any of the proteins described herein).

A description of other categories of useful agents and other individual agents can be found in Martindale, The Extra Pharmacopoeia, 30.sup.th Ed. (The Pharmaceutical Press, London 1993).

Examples of other agents that may be delivered using the device of the present invention include chlorhexidine, estradiol cypionate, estradiol valerate, flurbiprofen sodium, ivermectin, nafarelin, beta-glucan, bovine immunoglobulin, bovine superoxide dismutase, HIV-1 immunogen, human anti-TAC antibody, CD34 antibody, recombinant human growth hormone (r-hGH), recombinant human hemoglobin (r-Hb), recombinant human mecasermin (r-IGF-1), lenograstim (G-CSF), recombinant thyroid stimulating hormone (r-TSH), topotecan, aldesleukin, atenolol, epoetin alfa, leuprolide acetate, ceftriaxone, ceftazidime, oxaprozin, breveldin, valacyclovir, urofollitropin, famciclovir, flutamide, enalapril, mefformin, itraconazole, gabapentin, fosinopril, tramadol, lorazepan, follitropin, omeprazole, fluoxetine, lisinopril, tramsdol, levofloxacin, zafirlukast, growth hormone, granulocyte stimulating factor, nizatidine, bupropion, perindopril, erbumine, adenosine, alendronate, alprostadil, benazepril, bleomycin sulfate, dexfenfluramine, fentanyl, flecainid, gemcitabine, glatiramer acetate, granisetron, lamivudine, mangafodipir trisodium, mesalamine, metoprolol fumarate, miglitol, moexipril, monteleukast, octreotide acetate, olopatadine, paricalcitol, somatropin, sumatriptan succinate, tacrine, trovafloxac in, dolasetron, finasteride, Isradipine, lansoprazole, terbinafine, pamidronate, didanosine, cisapride, venlafaxine, fluvastatin, losartan, imiglucerase, donepezil, valsartan, fexofenadine, BCP 671, adapalene, doxazocin mesylate, mometasone furoate, ursodiol, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, rubitecan, amlodipine besylate/benazepril hydrochloride, etodolac, paroxetine hydrochloride, atovaquone, podofilox, betamethasone dipropionate, pramipexole dihydrochloride, Vitamin $D_3$ and related analogs, quetiapine fumarate, candesartan, cilexetil, fluconazole, ritonavir, flumazenil, carbemazepine, carbidopa, ganciclovir, saquinavir, amprenavir, sertraline hydrochloride, carved ilol, halobetasolproprionate, sildenafil citrate, chlorthalidone, imiquimod, simvastatin, citalopram, irinotecan hydrochloride, sparfloxacin, efavirenz, cisapride monohydrate, tamsulosin hydrochloride, mofafinil, letrozole, terbinafine hydrochloride, rosiglitazone maleate, diclofenac sodium, lomefloxacin hydrochloride, tirofiban hydrochloride, telmisartan, diazepam, loratadine, toremifene citrate, dinoprostone, mefloquine hydrochloride, trandolapril, tretinoin, nelfinavir mesylate, indinavir, beclomethasone dipropionate, isotretinoin, tamoxifen citrate, nimodipine, latanoprost, travoprost, unoprostone, AL-10682, AL-3138, AGN-191976, PhXA-34, AL-16082, bimatoprost, ethanolamide, dorzolamide, brinzolamide, acetazolamide, methazolamide, L-662583, MK-927, L-693612, L-685393, mannitol, glycerol, isosorbide, physostigamine, echothiophate, acetylcholine, methacholine, pilocarpine, aceclidine, carbachol, demecarium, isoflurophate, memantine, iomerizine, H-7, SR-43845, enalkiren, Y-39983, GPI-5693, anadamide, L-768242, L-759787, dexanabinol, collagenase ABC, iomefloxacin, iosartan, CS-088, mecobalamin, ISV-900, cardiotrophin-1, S-1033, D-22A, pentigetide, lerdelimumab, DE-085, SR-121463, org-34517, octamer, NNC-26-9100, KSR-592, A-75169, ethacrynate sodium, SDZ-GLC-756, rostaporfin, proxodolol, WIN-552122, OSA-8302, AL-16049, naboctate, L-696986, AL-4333A, vaninolol, PCA-50941, HGP-32, AGN-192836, AGN-191970, WP-934, ACC-9002, AL-4623A, L-4414A, CK-119, alprenoxime, CBT-101, AGN-191151, H 21644, SL 1111, GPI-5232, eliprodil, tilisolol, lomerizine, riluzole, lamotrigine, dextromethorphan, EAAT2, topiramate, AP5, CPP, selfotel or CGS 19755, CGP 37849, CGP 39551, CGP 40116, NPC 17742, aptiganel/CNS 1102, dextromethorphan and enzyme inhibitor, FR 115427, ketamine, ketobemidone, methadone, dizocilpine or MK 801, PCP, pethidine, RPR-1 19990, LY-300164 or talampanel, CNQX, DNQX, LY 215490, NNC 079202 or NBQX, NS 257, GYKI 52466, cyclothiazide, IDRA 21, DCG-IV, glycine, AP4, t-ACPD, L-SOP, L-AP3, S-4C3HPG, S-4CPG, MAP-4, RS-M4CPG, N-(3-[5-chloro-1-(4-chlorophenyl[indan-1-yl]propyl)-N-methylalanine, SR-57746A, T-588, 3,4 diaminopyridine, CPC-304, CPC-317, PD-176078, cephalosporin ceftriaxone, huperzine A, 10-methylhuperzine A, 10,10 dimethyl huperzine A, huperzine B, nicotine, epibaticline, cytosine, lobeline, anabasine, CNTF, BNDF, rhIGF-1, myotrophin mecasermin, Somatomedin C, GDNF, liatermin, neurturin, PEDF, FKBO-neuroimmunophilin ligands, AIT-082, leteprinim potassium, neotrofinT, emfilermin, CT-1, NT-3, NT-4/5, EHT 201, EHT 202, genistein, RX-77368, MK-771, JTP-2942, GPI-5000, ZVAD fink, 3-(2-phenyl-2-oxoethyl)-4,5-dimethylthiazolium salt, nordihydroguaiaretic acid, L-655238, Bay-X-1005, ML-3000, zileuton, oxothiazolidine carboxylate, ARR 17477, SOD, recombinant human CuZn-SOD, glutathione, glutathione peroxidase, catalase, nitric oxide synthase, vitamin E, vitamin C, selenium, acetylcysteine, seleginine, pycnogenol, co-enzyme Q10, beta carotene, PC 01, SC-55858, edaravone, iron (III) porphyrins, chromomycin, daunomycin, olivomycin, WP-631, DHEA, baclofen, tizandidine, dronabinol, diazepam, AVP-923, amitriptylene, fluvoxamine, sertraline, glycopyrrolate, copolamine, trihexyphenidyl, clonidine, propantheline, tropine, docusate sodium, tolterodine, TA-0910, ubiquinone, alpha lipoic acid, NAC, polyphenols, pregnenolone, threonine, methylcobalamin, metaxalone, tizanadine, carisoprodol, cyclobenzaprine, tramadol, potassium, calcium, zinc, magnesium, botulinum neurotoxin, succinylcholine, decamethonium, quinine, tetrahydrocannabinol, d-tubocurarine, atracurium, doxacurium, mivacurium, cistracurium besilate, pancuronium, pipecuronium bromide, rapacuronium bromide, rocuronium, vecuronium bromide, atracurium, suxamethonium; alcuronium, curare, metocurine, gallamine, nitrazepam, nordazepam, vigabatrin, procaine, chloroquine, gluthathione, odansetron, memantadine, GPI-1046, eradoline U-69 593, KW 6002, remacemide, dextromethorphan, NS-2214, CD133 antigen, CD34 antigen and reboxetine.

In addition to the above agents, there are a number of viruses, live or inactivate, including recombinant viruses that may, with the device of the present invention, be used to deliver nucleic acids to the vessel walls of a lumen. Treatment involves either the expression of a gene to provide a therapeutic effect to a cell or the expression of a gene to i) replace a mutated gene in a cell, ii) augment expression of a protein in a cell, or iii) inhibit a gene in a cell.

Of the therapeutic categories specified above, one set of preferred categories are those associated with treating retinal detachment that may or are likely to require the use of the present invention. Other preferred categories are those associated with the prevention or treatment of side effects (e.g., infection) possibly accompanying device insertion. Preferred therapeutic categories include hematological agents, preferably antiplatelet agents and anticoagulants; anti-infectives, preferably antimicrobials, antibacterials, antiviral agents, and antibiotics; immunobiologic agents, preferably immunosuppressives; proteins, preferably antibodies; cardiovascular agents, preferably anti-lipidemics, and thrombolytics/fibrinolytics; angiogenesis inhibitors; anti-apoptotics; antineoplastics; and collagen synthesis inhibitors.

The above agents may be used in any known pharmaceutically acceptable form. The term "pharmaceutically acceptable" refers to the agents being appropriate for use in vivo. For example, pharmaceutically acceptable forms include various metallic ion and organic ion forms. Metallic ions include, but are not limited to, alkali metal ions, alkaline earth metal ions and other physiological acceptable metal ions. Exemplary ions include aluminum, calcium, lithium, magnesium, potassium, sodium and zinc ion forms, where the ions are in their usual valences. Preferred organic ions include protonated tertiary amines and quatenary ammonium cations, including in part, trimethylamine, diethylamine, N,N'-dibenzylethylenediamine, chloroprocaine, choline, diethanolamine, ethylenediamine, meglumine (N-methylglucamine) and procaine.

Also included as pharmaceutically acceptable forms are various acid forms of the above agents. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, and benzoic acid. Further pharmaceutically acceptable forms include various salt forms of the above agents. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Other pharmaceutically acceptable salt forms are the base addition salt forms of the agents described above. Illustrative pharmaceutically acceptable base addition salts include metallic ion salts and organic ion salts. Preferred metallic ion salts include appropriate alkali metal (group Ia) salts, alkaline earth metal (group IIa) salts and other known physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine.

Also, other pharmaceutically acceptable forms of the above agents include the various isomeric forms (e.g., purified structural isomers; purified stereoisomers such as diastereomers and enantiomers; and purified racemates), tautomers, esters, amides and prodrugs of these agents.

Any one or more of the above-discussed agents may be coated onto the device or parts thereof parts of the device, in any conventional manner, such by a spray coating, vapor deposition, simple dip coating or, if a thicker coating of the therapeutic agent is desired, multiple dip coatings of the same or multiple agents. The agents may be applied directly onto the device in multiple layers.

Methods for spray coating a device are described, e.g., in U.S. Pat. Nos. 5,464,650 and 5,833,651. Alternatively, a thin film of a therapeutic agent may be molded over the device framework, as described in U.S. Pat. No. 4,866,062.

In general, multiple dipping involves applying several thin layers of the agent, while in liquid form (e.g., a solution, dispersion, or emulsion) of appropriate viscosity, and allowing each liquid layer to dry between successive applications. This method is typical in providing a timed release element of the drug to a device. Drying may be carried out simply by evaporation in air or promoted by heating, including baking or heat flashing, or even osmotic moisture removal, for example, by using a semipermeable membrane. Otherwise, the formation of a solid, adhering layer may be accomplished through chemical or biological transformations occurring on the device surface as described, for example in U.S. Pat. No. 4,548,736 where fibrin is solidified onto the device by carrying out the clotting reaction between fibrinogen and thrombin.

Active flow systems are also possible. For example, U.S. Pat. No. 6,153,252 describes a method using fluid flow or movement through the passages in a perforated medical device to avoid the formation of blockages or bridges. The fluid flow can be created by using a perforated manifold inserted in the device to circulate the coating fluid through the passages or by placing the device on a mandrel or in a small tube that is moved relative to the device during the coating process.

Another possibility for incorporation of a therapeutic agent is through the use of an active material that promotes physical or chemical adsorption. As described in WO 01/68158, an activated form of carbon known as a fullerene can promote the chemical binding of various biological agents (e.g., antibodies) to the surface of the rails 12, 12', 120 and 312 for therapeutic delivery. In the same manner, various materials described previously (e.g., polymeric materials) may be chemically modified, such as by the incorporation of a co-monomer, to introduce functional groups that chemically interact or bind to a given therapeutic agent.

It is contemplated that drug coatings can be incorporated into the individual strands prior to weaving into the fabric from which the device is manufactured. The use of strands comprising different active agents can be used in the same device. As a result, the devices according to the present invention permit customization of the agents delivered to the body by allowing different rail elements carrying the same or different agents to be introduced.

Additionally, a device manufactured from coated strands or coated fabric can be coated with additional layers of active agent after manufacture. The active agent can be coated over the entire device or only on portions thereof.

In yet another embodiment, the active agent may be released simultaneously by all strands or at completely different times or delivery may overlap in time. The release rates of the individual agents or of all agents can be customized for a particular patient or condition using biocompatible polymers and manufacturing methods described above. This would allow the delivery of drug to be optimized to the normal healing processes with the appropriate drug at the right concentration delivered at the desired point in time.

The agents applied in separate layers can be the same agent, different agents with different time releases or different agents intended to be released simultaneously or in successive order. In either instance, barrier layers can cover the different layers of agents. For example, a first barrier layer could cover the rail surface, a first drug layer could be applied on top of the barrier layer and a separation layer applied over the first drug layer. A second drug layer could be applied over the separation layer and then a cover layer could be applied over the second drug layer. More than two drug layers can be applied to the rails. The cover and separation layers can be chosen to provide predetermined and independent time release of the applied agents that they cover.

The different agents discussed above can be applied on different threads or portions of the device. As a result, numerous combinations of agents can be applied to the device. For example, each thread or coated portion of a rail can include one or more layers of the same or different agents. Hence, one rail could be coated with different agent combinations at different locations along its length.

Figure 8:
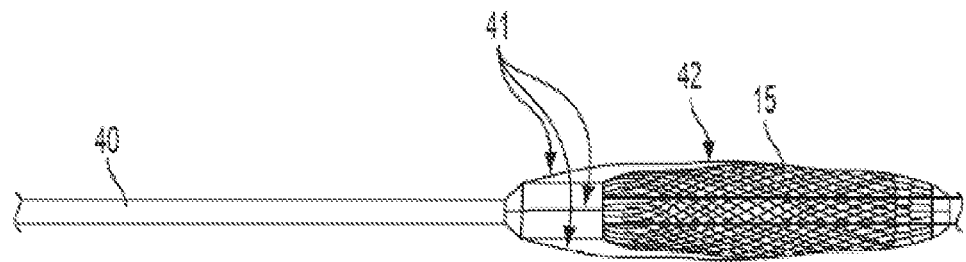
FIG. 8 is a side view of an embodiment of the present invention in an collapsed state inside a catheter

Once formed, and contracted, devices of the present invention may be loaded onto a delivery mechanism, such as a cannula for delivery into the eye. Referring to FIG. 8, the implant 15 is collapsed for loading into a cannula 42 for delivery into the eye. The implant is attached to guidewires 41 which are used to deploy the implant 15 and position it in place. The cannula can be a needle cannula which can be inserted with or without having to surgically cut into the eye. In a preferred embodiment the device is delivered through a cannula from 20 to 25 gage, most preferred through a cannula from 23 to 25 gage. Optionally the needle on the cannula is angled on the distal end to facilitate directing the implant to its intended location.

Figure 9:
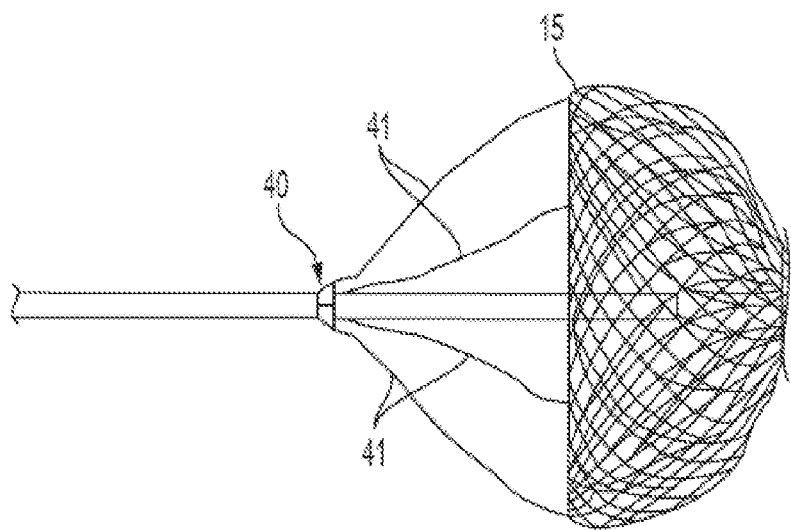
FIG. 9 is a side view of the embodiment in FIG. 8 in an expanded state.

FIG. 9 shows the device 15 of FIG. 8 in an expanded state following deployment cannula.

In an alternative embodiment, the device would be implanted into a syringe mechanism and directly injected into the eye.

In another embodiment the implant is positioned on a balloon prior to insertion in the cannula. The canula contains a lumen for inflating and deflating the balloon. The balloon may be inflated with an air or liquid source with a means for controlling. The air or liquid source is typically located outside the cannula. The implant is inserted into the eye with the cannula and guided into place at which point the balloon is inflated expanding the implant into position. The balloon is deflated, retracted into the cannula and the cannula removed from the eye. A vitrectomy will typically be performed to remove the vitreous humor from the eye prior to placing the device. Removal of the vitreous humor is done to allow room for expansion of the balloon. This is typically the initial step in any retinal repair procedure.

In yet another embodiment, the implant 15 is molded from a polymer. The polymer is preferably clear to allow light to pass through it.

The implants of the present invention may be any convenient shape which will allow the implant to exert sufficient force against the retina to hold it in position. Contemplated shapes include shapes which cover the hemisphere of the eye including the retina, less than half of the hemisphere of the eye and in some instances shapes which cover more than half the hemisphere of the eye.

Figure 11A:
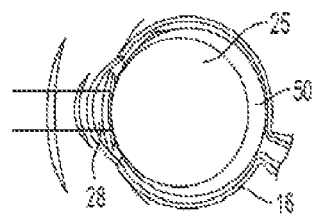
FIG. 11*a* is a side view of polymer device embodiment device detailing a continuous material covering the retinal tissue bed.

Referring to FIG. 11A, a polymeric implant 50 covering more than half the hemisphere of the eye is shown. In such an embodiment, it is important that the implant be comprised of a material which allows oxygen to pass through it. Preferably the material is optically clear so as not to obstruct vision.

Figure 11B:
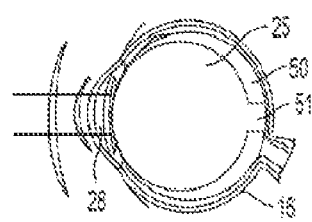
FIG. 11*b* is a side view of the polymer device embodiment detailing a through hole to the macula/fovea.

Depending on the transparency of the materials used, it may be desireable to include provide at least one opening for light to strike the retina. FIG. 11B shows another polymeric device of the present invention having an opening 51 exposing the fovea and macula.

Figure 11C:
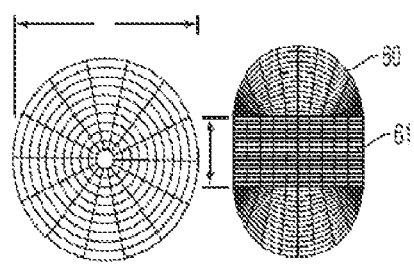
FIG. 11*c* shows side and end on views of the metallic embodiment of the device detailing globular support of the eye cavity with a through hole from the lens to the fovea/macula.
Figure 11D:
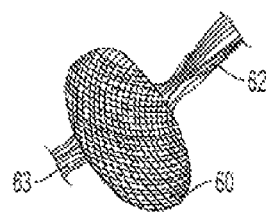
FIG. 11*d* shows a perspective view of the metallic embodiment of the device detailing a construction method to facilitate removal of the device from the eye cavity.

FIG. 11c shows a toroidal or spherical mesh implant 60 having a passageway 61 through the center for light to pass.F Method of Treatment Devices of the present invention can be readily inserted in a patient without the use of general anesthesia and with minimal trauma to the patient. Using this procedure the eye is anesthetized eliminating the need for general anesthesia in most instances. The device in its collapsed state would be inserted through a small needle cannula and/or through an optical scope through the sclera of the anesthetized eye. Upon exiting the distal segment of the delivery system, the surgeon will position the device and re-deploy it into its pre-programmed shape.

It is believed a surgeon implanting the present device will be able to do so by viewing the procedure through the lens under magnification. Depending on the materials employed, the device may be radio-opaque and capable of visualization through other commonly used imaging means such as Ultrasound, X-ray, Computerized Axial Tomography (CAT Scan) and Magnetic Resonance Imaging (MRI). The curvature of the device will aid in positing such that the implant will fit tightly against the retina wall with sufficient pressure to secure it against the inside of the eye. The delivery device is removed and if necessary, the entry hole is sutured.

In certain instances, it may be advantageous to remove the implant. In such instances the implant will further comprise a means for removal such as a tether, an eyelet, loop or bead which can be captured via a cannula delivered extraction tool or other specific device designed to capture and retrieve the stent. FIG. 11C shows a design having an extension 62 or 63 to facilitate removal. In such event, the tool would be delivered into the posterior chamber and the means for removal captured and the implant pulled into a cannula. In some instances it may be possible to retrieve the implant without the aid of a cannula.

The implants of the present invention may be used to alter the curvature of the eye thereby affecting the distance between the lens and the retina which would affect the focus of the eye. In normal vision the ciliary muscles surround the lens relax and contract thereby changing the curvature of the lens and thereby changing the focal length of the lens. This allows the eyes to focus on objects near and far. The implants of the present invention can be used to alter the curvature of the eye by implanting the device in a position which would elongate the globe. Myopia (nearsightedness) which results from the lens focusing the image in front of the retina can be treated by positioning the device at the back of the eye to stretch the globe in a manner which would pull the lens closer to the retina. Hyperopia (farsightedness) which results from the lens focusing the image behind the retina can be treated by positioning the implant on the sides of the eye would push the lens away from the implant. The implants used for vision correction can be specifically constructed to be wider, longer, and/or the curvature changed to achieve the desired change in shape so that vision correction is induced. It may also be possible to fabricate a device as described above such that the correction factor could be electronically controlled. This feature would allow the patient to have the device modify vision as Myopia or Hyperopia conditions change without the need for surgical intervention. There may also be the possibility to fabricate a device that combines both mechanisms for treatment of Myopia and Hyperopia into one device. This combination could be mechanical only or may combine an electronically controlled feature as previously described.

Figure 10A:
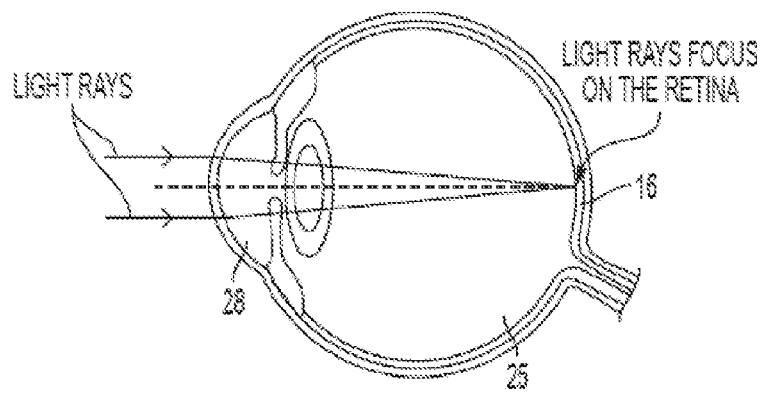
FIG. 10*a* shows a view of the optics of a normal eye.
Figure 10B:
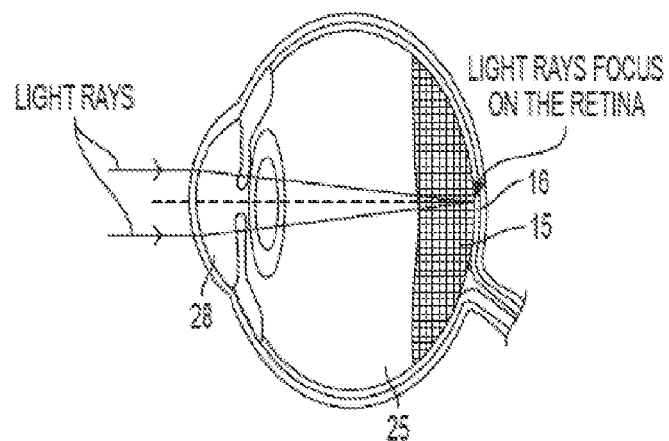
FIG. 10*b* shows a myopic eye corrected with the present invention.
Figure 10C:
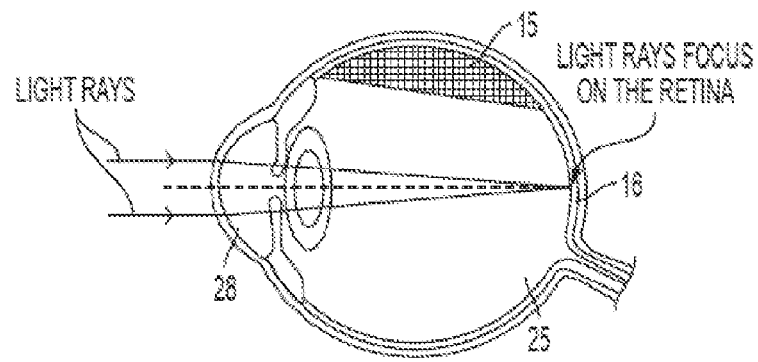
FIG. 10*c* shows a hyperopic eye corrected with the present invention.

FIG. 10a shows the optics of a normal eye in which the lens focuses directly on the retina. FIG. 10b shows a myopic eye in which implant 15 is implanted in the back of the posterior chamber to shorten the distance between the lens 28 and the retina 16 to correct nearsightedness. FIG. 10c shows a hyperopic eye in which the implant 15 has been implanted along the side of the posterior chamber to lengthen the distance between the lens 28 and the retina 16 to correct farsightedness. It will be apparent to one of skill in the art that multiple implants may be positioned While preferred embodiments of the present invention have been described, it will be readily appreciated by one of skill in the art that various changes, adaptations, modifications and use of multiple units of the present invention may be made without departing from the spirit of the invention and the scope of the claims.

We claim:

1. An implantable device for supporting a detached, torn or otherwise damaged retina within an eye comprising: a sufficiently curved structure sized to fit in the posterior chamber of the eye, wherein the support structure does not inhibit the transmission of images and;
   wherein the curved structure is made of metal or plastic and has a first expanded state and a second collapsed state, which in the collapsed state is deliverable to the retinal tissue for implant and in the expanded state conforms to the interior curvature of the eye in a manner which places appropriate force on the retinal tissue to hold it in place; and
   wherein the device is spheroid, wherein the device is designed to not touch the cornea.

2. The implantable device of claim 1 wherein the device is constructed as an essentially spheroid device that allows for the transmission of light.

3. The implantable device of claim 2, wherein the device is toroidal in shape.

4. The implantable device of claim 1 wherein the implantable device comprises a braided or woven material.

5. The implantable device of claim 4 wherein the material is a metallic composition.

6. The implantable device of claim 5 in which the device has a provision for anchoring directly into a specific section of the interior curve of the eye.

7. The implantable device of claim 4 wherein the material is a polymer composition.

8. The implantable device of claim 4 wherein the material is a metal and polymer hybrid composition.

9. The implantable device of claim 4 wherein the device is formed in an expanded state and is molded into a collapsed state for insertion into the posterior chamber.

10. The implantable device of claim 4 wherein the device may have a surface treatment intended to prevent adhesion to the tissue within the internal structure of the eye.

11. The implantable device of claim 10 wherein the surface treatment is a physical method of augmenting the surface of the device.

12. The implantable device of claim 10 wherein the surface treatment is a chemical method of augmenting the surface of the device.

13. The implantable device of claim 1 wherein the device is intended to be permanently implanted.

14. The implantable device of claim 1 wherein the devices further comprises a means for removal.

15. The implantable device of claim 14 wherein the means for removal comprises a tether for removal.

16. The implantable device of claim 14 wherein the means for removal is an eyelet, bead or closed loop.

17. The implantable device of claim 14 wherein the means for removal is a device designed to be selectively cut in specific points so that removal occurs in pieces.

18. The implantable device of claim 14 wherein the means for removal is/are specific sections of material that are dissolvable such that the device may be removed in several pieces.

19. The implantable device of claim 1 wherein the device comprises an absorbable polymer.

20. The implantable device of claim 1 wherein the polymer changes shape at set temperatures.

21. The implantable device of claim 1 wherein the implant is placed into its collapsed state during manufacturing by remolding the implant and setting it with temperature.

22. The implantable device of claim 1 wherein the device comprises a bioabsorbable polymer.

23. The implantable device of claim 22 wherein the bioabsorbable polymer comprises poly-l-lactic acid.

24. An implantable device for supporting a detached, torn or otherwise damaged retina within an eye comprising: a sufficiently curved structure sized to fit in the posterior chamber of the eye, wherein the support structure does not inhibit the transmission of images and;
   wherein the curved structure is made of metal or plastic and has a first expanded state and a second collapsed state, which in the collapsed state is deliverable to the retinal tissue for implant and in the expanded state conforms to the interior curvature of the eye in a manner which places appropriate force on the retinal tissue to hold it in place; and
   wherein the device expands to approximate a spheroid, such that the device produces an outward pressure sufficient to retain the retina or portions of the detached retina to the inner posterior portion of the eye.

25. The implantable device of claim 24 wherein the device is formed in an expanded state and is molded into a collapsed state for insertion into the posterior chamber.

26. The implantable device of claim 24 wherein the device is intended to be permanently implanted.

27. The implantable device of claim 24 wherein the devices further comprises a means for removal.

28. The implantable device of claim 27 wherein the means for removal comprises a tether for removal.

29. The implantable device of claim 27 wherein the means for removal is an eyelet, bead or closed loop.

30. The implantable device of claim 27 wherein the means for removal is a device designed to be selectively cut in specific points so that removal occurs in pieces.

31. The implantable device of claim 27 wherein the means for removal is/are specific sections of material that are dissolvable such that the device may be removed in several pieces.

32. The implantable device of claim 24 in which the device has a provision for anchoring directly into a specific section of the interior curve of the eye.

33. The implantable device of claim 24 wherein the device may have a surface treatment intended to prevent adhesion to the tissue within the internal structure of the eye.

34. The implantable device of claim 33 wherein the surface treatment is a physical method of augmenting the surface of the device.

35. The implantable device of claim 33 wherein the surface treatment is a chemical method of augmenting the surface of the device.

36. The implantable device of claim 24 wherein the device comprises a bioabsorbable polymer.

37. The implantable device of claim 36 wherein the bioabsorbable polymer comprises poly-l-lactic acid.

* * * * *